United States Patent [19]

Makoff et al.

[11] Patent Number: 5,389,540

[45] Date of Patent: Feb. 14, 1995

[54] EXPRESSION OF TETANUS TOXIN FRAGMENT C IN YEAST

[75] Inventors: Andrew J. Makoff; Michael A. Romanos; Jeffrey J. Clare; Neil F. Fairweather, all of Beckenham, England

[73] Assignee: Evans Medical Limited, Leatherhead, United Kingdom

[21] Appl. No.: 618,312

[22] Filed: Nov. 27, 1990

[30] Foreign Application Priority Data

Nov. 28, 1989 [GB] United Kingdom ................ 8926832
Mar. 17, 1990 [GB] United Kingdom ................ 9006097

[51] Int. Cl.$^6$ ................ A61K 39/08; C12N 15/31; C12N 15/67
[52] U.S. Cl. ................ 435/69.3; 424/88; 424/190.1; 424/261.1; 435/69.1; 435/172.3; 435/252.3; 435/254.11; 435/254.2; 435/254.21; 435/320.1; 536/23.1; 536/23.7
[58] Field of Search ............ 424/88; 435/69.1, 172.3, 435/252.3; 536/27

[56] References Cited

U.S. PATENT DOCUMENTS 4,007,265  2/1977  Helting ........................ 424/92

FOREIGN PATENT DOCUMENTS 1492596  11/1974  United Kingdom .

OTHER PUBLICATIONS

Bitter, G. A. et al. (1984) Gene 32: 263–274.
Fairweather, N. F. et al (1986) J. Bacteriology 165: 21–27.
Zaret, K. S. et al (1982) Cell 28: 563–573.
Makoff, A. J. et al (1989) Biotechnology 7: 1043–1046.
Weller, U. (1989) Eur. J. Biochem. 182: 649–656.
Fairweather, N. F. (1986) Nucleic Acids Res. 14: 7809–7812.
Osborne, B. I. et al (1989) Proc. Natl. Acad. Sci USA 86: 4097–4101.
Kingsman, S. M. et al (1985) Biotechnology & Genetic Eng. Reviews 3: 377–416.
Bennetzen, J. L. et al (1982) J. Biol. Chem. 257: 3018–3025.
Bennetzen, J. L. et al. (82) J. Biol. Chem. 275: 3026–3031.
Robinson, M. et al (84) Nucleic Acids Res. 12: 6663–6671.
Gouy, M. et al. (82) Nucleic Acids Res 10: 7055–7074.
Williams, D. P. et al (88) Nucleic Acids Res. 16: 10453–10467.
Sharp, P. M. et al. (88) Nucleic Acids Res. 16: 8207–8241.
Eur J. Biochem. 156, 413–321 FEBS 1986 Belsham et al "Expression of polyoma virus middle-T antigen in Saccharomyces cerevisiae".
Yeast vol. 5: 187–198 (1989) Bettany et al "5'-Secondary Structure Formation in Contrast to a Short . . . in Yeast".
Gene 16 (1987) 265–275 Elsevier Cousens et al "High Level expression of proinsulin in the yeast, Saccharomyces cerevisiae".
TIBTECH-Aug. 1988 vol. 6, 196–199 Ernst "Codon usage and gene expression".

(List continued on next page.)

Primary Examiner—Christine M. Nucker
Assistant Examiner—Michael S. Tuscan
Attorney, Agent, or Firm—Nixon & Vanderhye

[57] ABSTRACT

Expression of tetanus toxin fragment C is accomplished employing a DNA coding sequence having a (G+C)-content that has been increased in the region from nucleotide 410 to the 3' end of the coding sequence relative to the wild-type DNA sequence. This allows the production of complete mRNA transcripts. Typically the (G+C)-content is increased in the following regions: (i) nucleotides 510–710, (ii) nucleotides 650–850, (iii) nucleotides 800–1100, (iv) nucleotides 900–1200 and (v) nucleotides 1100 to the 3' end of the coding sequence. The (G+C)-content may also be increased in the region of nucleotides 410–610. These regions in the wild-type DNA encompass terminator sequences.

3 Claims, 24 Drawing Sheets

OTHER PUBLICATIONS

Gene 46 (1986) 135–141 Kniskern et al "Unusually high-level expression of a foreign gene . . . Saccharomyces cerevisiae".

Yeast vol. 5: 497–507 (1989) Loison et al "High Level of Expression of a Protective Antigen of Schistosomes in Saccharomyces cerevisiae".

Nucleic Acids Research vol. 17 No. 24, 1989, 10191–10202 Makoff et al "Expression of tetanus toxin fragment C in E. coli: high . . . codoms".

Proc. Natl. Acad. Sci. USA vol. 82, 7232–7236 Nov. 1985 Miyamoto et al "Molecular cloning and regulated expression in the human . . . products".

Proc. Natl. Acad. Sci. USA vol. 80, 7461–7465 Dec. 1983 Biochemistry Urdea et al "Chemical synthesis of a gene for human . . . in yeast".

Fig. 2A

```
                                          30                                        60                                        90
ATG AAA AAT CTG GAT TGT TGG GTT GAT AAT GAA GAA GAT ATA GAT GTT ATA AAA AAG AGT ACA ATT TTA AAT TTA GAT ATT AAT AAT
      C   T                         C       C                     C C G               TC     C   C G     C   C   C
Met Lys Asn Leu Asp Cys Trp Val Asp Asn Glu Glu Asp Ile Asp Val Ile Lys Lys Ser Thr Ile Leu Asn Leu Asp Ile Asn Asn
                                                            120                    BanI              150                        180
GAT ATT ATA TCA GAT ATA TCT GGG TTT AAT TCA TCT GTA ATA ACA TAT CCA GAT GCT CAA TTG GTG CCC GGA ATA AAT GGC AAA GCA ATA
                C   C   C           T   C   C           T   C                                       G   C   C           T   C
Asp Ile Ile Ser Asp Ile Ser Gly Phe Asn Ser Ser Val Ile Thr Tyr Pro Asp Ala Gln Leu Val Pro Gly Ile Asn Gly Lys Ala Ile
                                         210                                       240                                       270
CAT TTA GTA AAC AAT GAA TCT TCT GAA GTT ATA GTG CAT AAA GCT ATG GAT ATT GAA TAT AAT AAT TTT AAT AAT TTT ACC GTT AGC
    C C C           T C                         C                 C   C G       C                 C   C   C       AGC
His Leu Val Asn Asn Glu Ser Ser Glu Val Ile Val His Lys Ala Met Asp Ile Glu Tyr Asn Asp Met Phe Asn Asn Phe Thr Val Ser
                                       300                                       330                                         360
TTT TGG TTG AGG GTT CCT AAA GTA TCT GCT AGT CAT TTA GAA CAA CAA AAT GGC ACA TAT GAG TAT TCA ATA ATT AGC TCT ATG AAA AAA CAT
  C   C   C           G       T                 TCC C C C                 G           C         C   C                 G
Phe Trp Leu Arg Val Pro Lys Val Ser Ala Ser His Leu Glu Gln Gln Asn Gly Thr Tyr Glu Tyr Ser Ile Ile Ser Ser Met Lys Lys His
                                       390                                       420                   SacII              450
AGT CTA TCA ATA GGA TCT GGT TGG AGT GTA TCA CTT AAA GGT AAT AAC TTA ATA TGG ACT TTA AAA GAT TCC GCG GGA GAA GTT AGA CAA
TCC   G   C   C                 TC   T   C                     C   C G           C           C G             C   CT G
Ser Leu Ser Ile Gly Ser Gly Trp Ser Val Ser Leu Lys Gly Asn Asn Leu Ile Trp Thr Leu Lys Asp Ser Ala Gly Glu Val Arg Gln
                                       480                                       510                                         540
ATA ACT TTT AGG GAT TTA CCT GAT AAA TTT AAT GCT TAT TTA GCA AAT AAA TGG GTT TTT ATA ACT ATT AAT GAT AGA TTA TCT TCT
  C       C   C   C C G   G     C   C G   C   C     C   C   C C G   T   C                   C       C   C   CT C G
Ile Thr Phe Arg Asp Leu Pro Asp Lys Phe Asn Ala Tyr Leu Ala Asn Lys Trp Val Phe Ile Thr Ile Asn Asp Arg Leu Ser Ser
```

Fig. 2B

```
                                570                         600                               630
GCT AAT TTG TAT ATA AAT GGA GTA CTT ATG GGA AGT GCA GAA ATT ACT GGT TTA GGA GCT ATT AGA GAG GAT AAT AAT ATA ACA TTA AAA
    C   C   C       C       T   G           C   T       C           C   G               C   C   C   C       T   C   T   G
Ala Asn Leu Tyr Ile Asn Gly Val Leu Met Gly Ser Ala Glu Ile Thr Gly Leu Gly Ala Ile Arg Glu Asp Asn Asn Ile Thr Leu Lys

MaeII                 690                                           720
CTA GAT AGA TGT AAT AAT AAT CAA TAC GTT TCT ATT GAT AAA TTT AGG ATA TTT TGC AAA GCA TTA AAT CCA AAA GAG ATT GAA AAA
    G       C C T       C   C   C       A   C   C   G       C C T               C G       C G   C   G                 C
Leu Asp Arg Cys Asn Asn Asn Gln Tyr Val Ser Ile Asp Lys Phe Arg Ile Phe Cys Lys Ala Leu Asn Pro Lys Glu Ile Glu Lys 750                         780                                           810
TTA TAC ACA AGT TAT TTA TCT ATA ACC TTT TTA AGA GAC TTC TGG GGA AAC CCT TTA CGA TAT GAT ACA GAA TAT TAT TTA ATA CCA GTA
C G T       C   C   C C G       C                   T               C C G C T           G C G   T   C   C       C C G   G
Leu Tyr Thr Ser Tyr Leu Ser Ile Thr Phe Leu Arg Asp Phe Trp Gly Asn Pro Leu Arg Tyr Asp Thr Glu Tyr Tyr Leu Ile Pro Val 840                         870                                           900
GCT TCT AGT TCT AAA GAT GTT CAA TTG AAA AAT ATA ACA GAT TAT ATG TAT TTG ACA AAT GCG CCA TCG TAT ACT AAC GGA AAA TTG AAT
    C   C       C   G C   C C   C           G C           C   C   C   C   C               C   C   G   C       T   C   C
Ala Ser Ser Lys Asp Val Gln Leu Lys Asn Ile Thr Asp Tyr Met Tyr Leu Thr Asn Ala Pro Ser Tyr Thr Asn Gly Lys Leu Asn 930                         960                         HinfI             990
ATA TAT TAT AGA AGG TTA TAT AAT GGA CTA AAA TTT ATT ATA AAA AGA TAT ACA CCT AAT AAT GAA ATA GAT TCT TTT GTT AAA TCA GGT
C   C   C   C   CTCG   C   C       G   C   C   C   C   C       C   C   C C T   G   C   C       C               C   T
Ile Tyr Tyr Arg Arg Leu Tyr Asn Gly Leu Lys Phe Ile Ile Lys Arg Tyr Thr Pro Asn Asn Glu Ile Asp Ser Phe Val Lys Ser Gly
```

Fig. 2C

```
                                              1020                                  1050
GAT TTT ATT AAA TTA TAT GTA TCA TAT AAC AAT GAG CAC ATT GTA GGT TAT CCG AAA GAT GGA AAT GCC TTT AAT AAT CTT GAT AGA
 C   C       C G   C   T     C  C  T  C       A   C       C       T   C       C  T  C  C  G   C
Asp Phe Ile Lys Leu Tyr Val Ser Tyr Asn Asn Glu His Ile Val Gly Tyr Pro Lys Asp Gly Asn Ala Phe Asn Asn Leu Asp Arg 1110                                  1140                      1170
ATT CTA AGA GTA GGT TAT AAT GCC CCA GGT ATC CCT CTT TAT AAA AAA ATG GAA GCA GTA AAA TTG CGT GAT TTA AAA ACC TAT TCT GTA
     G  C T   C  C       T   C  C  T  G       G  G  C               T   C            C     C  C G        C     T
Ile Leu Arg Val Gly Tyr Asn Ala Pro Gly Ile Pro Leu Tyr Lys Lys Met Glu Ala Val Lys Leu Arg Asp Leu Lys Thr Tyr Ser Val 1200                                  1230                      1260
CAA CTT AAA TTA TAT GAT AAA AAT GCA TCT TTA GGA CTA GTA GGT ACC CAT AAT GGT CAA ATA GGC AAC GAT CCA AAT AGG GAT ATA
 G   G       C G   C  C  C       C       T   C G        T  G  T   C  C       G   C  T    C   G   C  C C T   C   C
Gln Leu Lys Leu Tyr Asp Lys Asn Ala Ser Leu Gly Leu Val Gly Thr His Asn Gly Gln Ile Gly Asn Asp Pro Asn Arg Asp Ile 1290                                  1320                      1350
TTA ATT GCA AGC AAC TGG TAC TTT AAT CAT TTA AAA GAT AAA ATT TTA GGA TGT GAT TGG TAC TTT GTA CCT ACA GAT GAA GGA TGG ACA
 C G   C   T TCT                    C   C   C C G    C         C  C G        T  C  C        C     T G  C       T     C
Leu Ile Ala Ser Asn Trp Tyr Phe Asn His Leu Lys Asp Lys Ile Leu Gly Cys Asp Trp Tyr Phe Val Pro Thr Asp Glu Gly Trp Thr

AAT GAT TAA
 C   C
Asn Asp ...
```

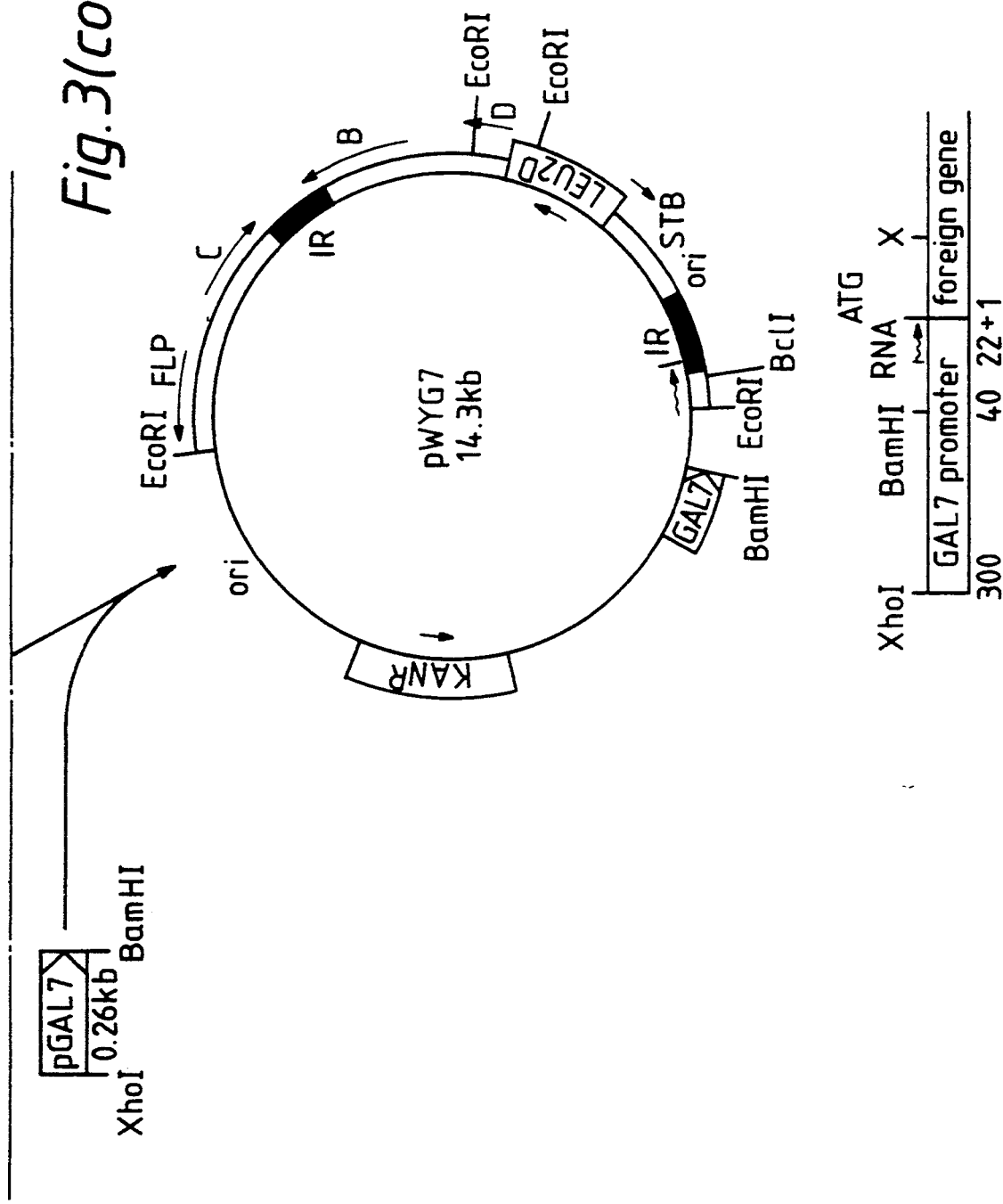

Fig.4.

```
            10         20         30         40         50         60
Xho I       *          *          *          *          *          *
CTCGAGACGT CTATACTTCG GAGCACTGTT GAGCGAAGGC TCATTAGATA TATTTTCTGT
GAGCTCTGCA GATATGAAGC CTCGTGACAA CTCGCTTCCG AGTAATCTAT ATAAAAGACA 70         80         90        100        110        120
            *          *          *          *          *          *
CATTTTCCTT AACCCAAAAA TAAGGGAGAG GGTCCAAAAA GCGCTCGGAC AACTGTTGAC
GTAAAAGGAA TTGGGTTTTT ATTCCCTCTC CCAGGTTTTT CGCGAGCCTG TTGACAACTG 130        140        150        160        170        180
            *          *          *          *          *          *
CGTGATCCGA AGGACTGGCT ATACAGTGTT CACAAAATAG CCAAGCTGAA AATAATGTGT
GCACTAGGCT TCCTGACCGA TATGTCACAA GTGTTTTATC GGTTCGACTT TTATTACACA 190        200        210        220        230        240
            *          *          *          *          *          *
AGCCTTTAGC TATGTTCAGT TAGTTTGGCT AGCAAAGATA TAAAAGCAGG TCGGAAATAT
TCGGAAATCG ATACAAGTCA ATCAAACCGA TCGTTTCTAT ATTTTCGTCC AGCCTTTATA 250        260        270        280        290        300
            *          *   Bam HI *          *        ↓ *          *
TTATGGGCAT TATTATGCAG AGGATCCACA TGATAAAAAA AACAGTTGAA TATTCCCTCA
AATACCCGTA ATAATACGTC TCCTAGGTGT ACTATTTTTT TTGTCAACTT ATAAGGGAGT

310
            *          *
AAAATGACTG
TTTTACTGAC
```

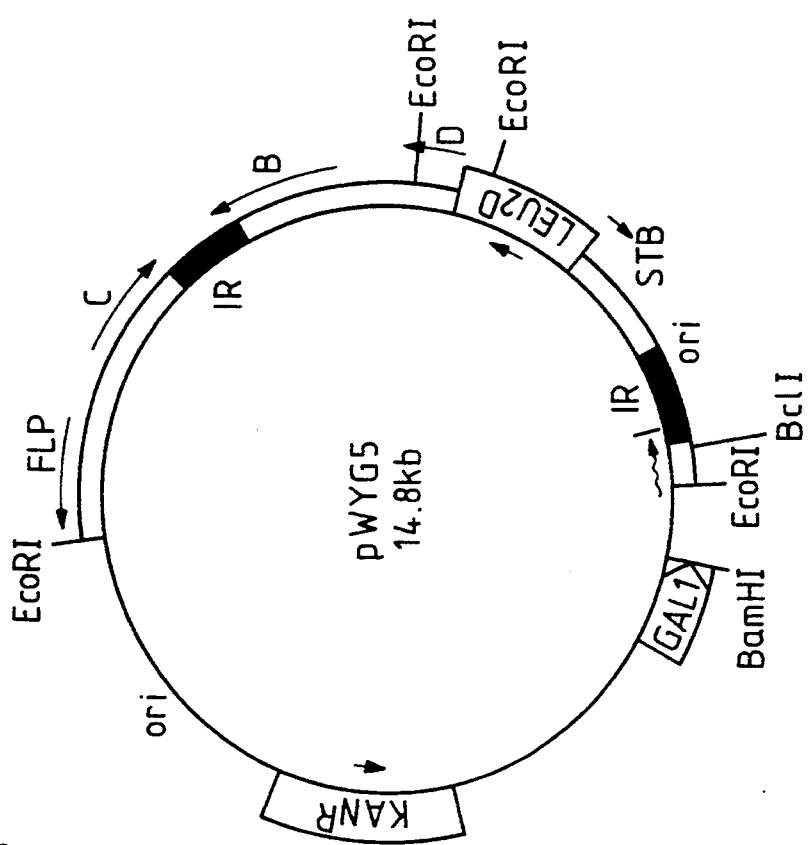
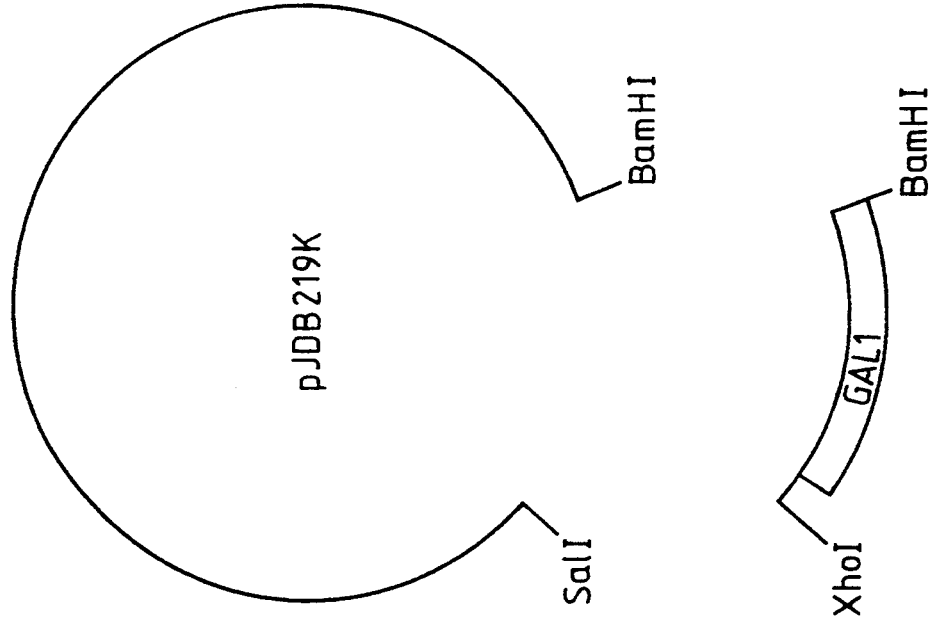
Fig. 5B

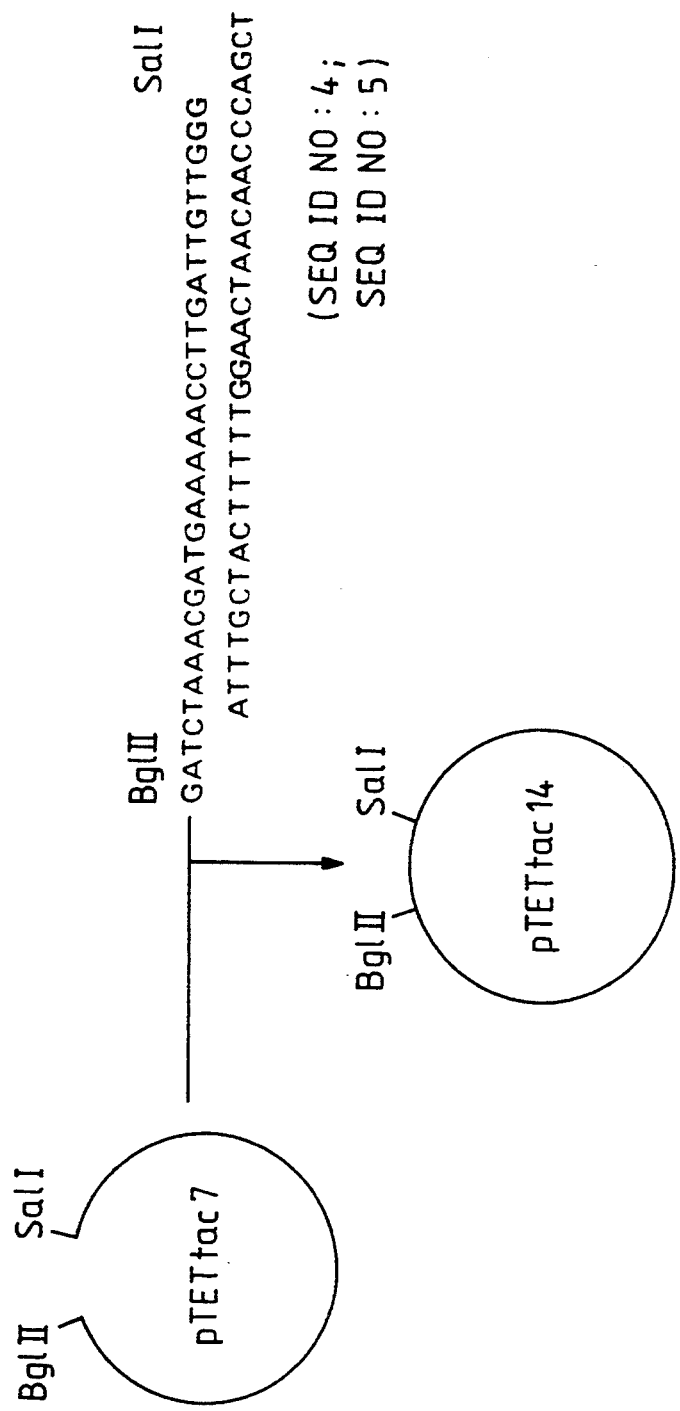

Construction of pIC-TET

Construction of pTETtac16

Fig.13(cont.)

```
           130               140               150               160               170
            *                 *                 *                 *                 *
TAC TCA GAT TTA GAA GGG GAT TTC GAT GTT GCT GTT CAA TTG CCA TTT TCC AAC
ATG AGT CTA AAT CTT CCC CTA AAG CTA CGA CAA CAA AAC GGT AAA AGG TTG
Tyr Ser Asp Leu Glu Gly Asp Phe Asp Val Ala Val Leu Pro Phe Ser Asn 180               190               200               210               220
            *                 *                 *                 *                 *
AGC ACA AAT AAC GGG TTA TTG TTT ATA AAT ACT ACT ATT GCC AGC ATT GCT
TCG TGT TTA TTG CCC AAT AAC AAA TAT TGA TGA TAA CGG TCG TAA CGA
Ser Thr Asn Asn Gly Leu Leu Phe Ile Asn Thr Thr Ile Ala Ser Ile Ala 230               240               250               260               270
            *                 *   XhoI            *                 *   NcoI    *
GCT AAA GAA GAA GGG GTA TCT CTC GAG AAA AGA GAG GCT GAA GCC
CGA TTT CTT CTT CCC CAT AGA GAG CTC TTT TCT CTC CGA CTT CGG TAC C
Ala Lys Glu Glu Gly Val Ser Leu Glu Lys Arg Glu Ala Glu Ala Met>
```

(SEQ ID NO : 9;
SEQ ID NO : 10)

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 1359 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( v i ) ORIGINAL SOURCE:
( A ) ORGANISM: Clostridium tetani ( i x ) FEATURE:
( A ) NAME/KEY: CDS
( B ) LOCATION: 1..1356

( x i ) SEQUENCE DESCRIPTION: SEQ ID NO:1:

```
ATG AAA AAT CTG GAT TGT TGG GTT GAT AAT GAA GAA GAT ATA GAT GTT      48
Met Lys Asn Leu Asp Cys Trp Val Asp Asn Glu Glu Asp Ile Asp Val
  1               5                  10                  15

ATA TTA AAA AAG AGT ACA ATT TTA AAT TTA GAT ATT AAT AAT GAT ATT      96
Ile Leu Lys Lys Ser Thr Ile Leu Asn Leu Asp Ile Asn Asn Asp Ile
             20                  25                  30

AAT ATC GAT ATA TCT GGG TTT AAT TCA TCT GTA ATA ACA TAT CCA GAT     144
Asn Ile Asp Ile Ser Gly Phe Asn Ser Ser Val Ile Thr Tyr Pro Asp
         35                  40                  45

GCT CAA TTG GTG CCC GGA ATA AAT GGC AAA GCA ATA CAT TTA GTA AAC     192
Ala Gln Leu Val Pro Gly Ile Asn Gly Lys Ala Ile His Leu Val Asn
     50                  55                  60

AAT GAA TCT TCT GAA GTT ATA GTG CAT AAA GCT ATG GAT ATT GAA TAT     240
Asn Glu Ser Ser Glu Val Ile Val His Lys Ala Met Asp Ile Glu Tyr
 65                  70                  75                  80

AAT GAT ATG TTT AAT AAT TTT ACC GTT AGC TTT TGG TTG AGG GTT CCT     288
Asn Asp Met Phe Asn Asn Phe Thr Val Ser Phe Trp Leu Arg Val Pro
                 85                  90                  95

AAA GTA TCT GCT AGT CAT TTA GAA CAA TAT GGC ACA AAT GAG TAT TCA     336
Lys Val Ser Ala Ser His Leu Glu Gln Tyr Gly Thr Asn Glu Tyr Ser
            100                 105                 110
```

| | | | | | | | | | | | | | | | | |
|---|---|---|---|---|---|---|---|---|---|---|---|---|---|---|---|---|
| ATA | ATT | AGC | TCT | ATG | AAA | AAA | CAT | AGT | CTA | TCA | ATA | GGA | TCT | GGT | TGG | 384 |
| Ile | Ile | Ser | Ser | Met | Lys | Lys | His | Ser | Leu | Ser | Ile | Gly | Ser | Gly | Trp | |
| | | 115 | | | | | 120 | | | | | 125 | | | | |
| AGT | GTA | TCA | CTT | AAA | GGT | AAT | AAC | TTA | ATA | TGG | ACT | TTA | AAA | GAT | TCC | 432 |
| Ser | Val | Ser | Leu | Lys | Gly | Asn | Asn | Leu | Ile | Trp | Thr | Leu | Lys | Asp | Ser | |
| | 130 | | | | | 135 | | | | | 140 | | | | | |
| GCG | GGA | GAA | GTT | AGA | CAA | ATA | ACT | TTT | AGG | GAT | TTA | CCT | GAT | AAA | TTT | 480 |
| Ala | Gly | Glu | Val | Arg | Gln | Ile | Thr | Phe | Arg | Asp | Leu | Pro | Asp | Lys | Phe | |
| 145 | | | | | 150 | | | | | 155 | | | | | 160 | |
| AAT | GCT | TAT | TTA | GCA | AAT | AAA | TGG | GTT | TTT | ATA | ACT | ATT | ACT | AAT | GAT | 528 |
| Asn | Ala | Tyr | Leu | Ala | Asn | Lys | Trp | Val | Phe | Ile | Thr | Ile | Thr | Asn | Asp | |
| | | | | 165 | | | | | 170 | | | | | 175 | | |
| AGA | TTA | TCT | TCT | GCT | AAT | TTG | TAT | ATA | AAT | GGA | GTA | CTT | ATG | GGA | AGT | 576 |
| Arg | Leu | Ser | Ser | Ala | Asn | Leu | Tyr | Ile | Asn | Gly | Val | Leu | Met | Gly | Ser | |
| | | | 180 | | | | | 185 | | | | | 190 | | | |
| GCA | GAA | ATT | ACT | GGT | TTA | GGA | GCT | ATT | AGA | GAG | GAT | AAT | AAT | ATA | ACA | 624 |
| Ala | Glu | Ile | Thr | Gly | Leu | Gly | Ala | Ile | Arg | Glu | Asp | Asn | Asn | Ile | Thr | |
| | | | 195 | | | | | 200 | | | | | 205 | | | |
| TTA | AAA | CTA | GAT | AGA | TGT | AAT | AAT | AAT | AAT | CAA | TAC | GTT | TCT | ATT | GAT | 672 |
| Leu | Lys | Leu | Asp | Arg | Cys | Asn | Asn | Asn | Asn | Gln | Tyr | Val | Ser | Ile | Asp | |
| | 210 | | | | | 215 | | | | | 220 | | | | | |
| AAA | TTT | AGG | ATA | TTT | TGC | AAA | GCA | TTA | AAT | CCA | AAA | GAG | ATT | GAA | AAA | 720 |
| Lys | Phe | Arg | Ile | Phe | Cys | Lys | Ala | Leu | Asn | Pro | Lys | Glu | Ile | Glu | Lys | |
| 225 | | | | | 230 | | | | | 235 | | | | | 240 | |
| TTA | TAC | ACA | AGT | TAT | TTA | TCT | ATA | ACC | TTT | TTA | AGA | GAC | TTC | TGG | GGA | 768 |
| Leu | Tyr | Thr | Ser | Tyr | Leu | Ser | Ile | Thr | Phe | Leu | Arg | Asp | Phe | Trp | Gly | |
| | | | | 245 | | | | | 250 | | | | | 255 | | |
| AAC | CCT | TTA | CGA | TAT | GAT | ACA | GAA | TAT | TAT | TTA | ATA | CCA | GTA | GCT | TCT | 816 |
| Asn | Pro | Leu | Arg | Tyr | Asp | Thr | Glu | Tyr | Tyr | Leu | Ile | Pro | Val | Ala | Ser | |
| | | | 260 | | | | | 265 | | | | | 270 | | | |
| AGT | TCT | AAA | GAT | GTT | CAA | TTG | AAA | AAT | ATA | ACA | GAT | TAT | ATG | TAT | TTG | 864 |
| Ser | Ser | Lys | Asp | Val | Gln | Leu | Lys | Asn | Ile | Thr | Asp | Tyr | Met | Tyr | Leu | |
| | | 275 | | | | | 280 | | | | | 285 | | | | |
| ACA | AAT | GCG | CCA | TCG | TAT | ACT | AAC | GGA | AAA | TTG | AAT | ATA | TAT | TAT | AGA | 912 |
| Thr | Asn | Ala | Pro | Ser | Tyr | Thr | Asn | Gly | Lys | Leu | Asn | Ile | Tyr | Tyr | Arg | |
| | 290 | | | | | 295 | | | | | 300 | | | | | |
| AGG | TTA | TAT | AAT | GGA | CTA | AAA | TTT | ATT | ATA | AAA | AGA | TAT | ACA | CCT | AAT | 960 |
| Arg | Leu | Tyr | Asn | Gly | Leu | Lys | Phe | Ile | Ile | Lys | Arg | Tyr | Thr | Pro | Asn | |
| 305 | | | | | 310 | | | | | 315 | | | | | 320 | |
| AAT | GAA | ATA | GAT | TCT | TTT | GTT | AAA | TCA | GGT | GAT | TTT | ATT | AAA | TTA | TAT | 1008 |
| Asn | Glu | Ile | Asp | Ser | Phe | Val | Lys | Ser | Gly | Asp | Phe | Ile | Lys | Leu | Tyr | |
| | | | | 325 | | | | | 330 | | | | | 335 | | |
| GTA | TCA | TAT | AAC | AAT | AAT | GAG | CAC | ATT | GTA | GGT | TAT | CCG | AAA | GAT | GGA | 1056 |
| Val | Ser | Tyr | Asn | Asn | Asn | Glu | His | Ile | Val | Gly | Tyr | Pro | Lys | Asp | Gly | |
| | | | 340 | | | | | 345 | | | | | 350 | | | |
| AAT | GCC | TTT | AAT | AAT | CTT | GAT | AGA | ATT | CTA | AGA | GTA | GGT | TAT | AAT | GCC | 1104 |
| Asn | Ala | Phe | Asn | Asn | Leu | Asp | Arg | Ile | Leu | Arg | Val | Gly | Tyr | Asn | Ala | |
| | | 355 | | | | | 360 | | | | | 365 | | | | |
| CCA | GGT | ATC | CCT | CTT | TAT | AAA | AAA | ATG | GAA | GCA | GTA | AAA | TTG | CGT | GAT | 1152 |
| Pro | Gly | Ile | Pro | Leu | Tyr | Lys | Lys | Met | Glu | Ala | Val | Lys | Leu | Arg | Asp | |
| | 370 | | | | | 375 | | | | | 380 | | | | | |
| TTA | AAA | ACC | TAT | TCT | GTA | CAA | CTT | AAA | TTA | TAT | GAT | GAT | AAA | AAT | GCA | 1200 |
| Leu | Lys | Thr | Tyr | Ser | Val | Gln | Leu | Lys | Leu | Tyr | Asp | Asp | Lys | Asn | Ala | |
| 385 | | | | | 390 | | | | | 395 | | | | | 400 | |
| TCT | TTA | GGA | CTA | GTA | GGT | ACC | CAT | AAT | GGT | CAA | ATA | GGC | AAC | GAT | CCA | 1248 |
| Ser | Leu | Gly | Leu | Val | Gly | Thr | His | Asn | Gly | Gln | Ile | Gly | Asn | Asp | Pro | |
| | | | | 405 | | | | | 410 | | | | | 415 | | |
| AAT | AGG | GAT | ATA | TTA | ATT | GCA | AGC | AAC | TGG | TAC | TTT | AAT | CAT | TTA | AAA | 1296 |
| Asn | Arg | Asp | Ile | Leu | Ile | Ala | Ser | Asn | Trp | Tyr | Phe | Asn | His | Leu | Lys | |
| | | | 420 | | | | | 425 | | | | | 430 | | | |
| GAT | AAA | ATT | TTA | GGA | TGT | GAT | TGG | TAC | TTT | GTA | CCT | ACA | GAT | GAA | GGA | 1344 |
| Asp | Lys | Ile | Leu | Gly | Cys | Asp | Trp | Tyr | Phe | Val | Pro | Thr | Asp | Glu | Gly | |

|             |             |             |
|:-----------:|:-----------:|:-----------:|
|     435     |     440     |     445     |

TGG ACA AAT GAT TAA                                                          1359
Trp Thr Asn Asp
    450

( 2 ) INFORMATION FOR SEQ ID NO:2:

( i ) SEQUENCE CHARACTERISTICS:
        ( A ) LENGTH: 452 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Lys Asn Leu Asp Cys Trp Val Asp Asn Glu Glu Asp Ile Asp Val
 1               5                  10                  15
Ile Leu Lys Lys Ser Thr Ile Leu Asn Leu Asp Ile Asn Asn Asp Ile
                20                  25                  30
Asn Ile Asp Ile Ser Gly Phe Asn Ser Ser Val Ile Thr Tyr Pro Asp
            35                  40                  45
Ala Gln Leu Val Pro Gly Ile Asn Gly Lys Ala Ile His Leu Val Asn
        50                  55                  60
Asn Glu Ser Ser Glu Val Ile Val His Lys Ala Met Asp Ile Glu Tyr
 65                  70                  75                  80
Asn Asp Met Phe Asn Asn Phe Thr Val Ser Phe Trp Leu Arg Val Pro
                85                  90                  95
Lys Val Ser Ala Ser His Leu Glu Gln Tyr Gly Thr Asn Glu Tyr Ser
                100                 105                 110
Ile Ile Ser Ser Met Lys Lys His Ser Leu Ser Ile Gly Ser Gly Trp
            115                 120                 125
Ser Val Ser Leu Lys Gly Asn Asn Leu Ile Trp Thr Leu Lys Asp Ser
        130                 135                 140
Ala Gly Glu Val Arg Gln Ile Thr Phe Arg Asp Leu Pro Asp Lys Phe
145                 150                 155                 160
Asn Ala Tyr Leu Ala Asn Lys Trp Val Phe Ile Thr Ile Thr Asn Asp
                165                 170                 175
Arg Leu Ser Ser Ala Asn Leu Tyr Ile Asn Gly Val Leu Met Gly Ser
                180                 185                 190
Ala Glu Ile Thr Gly Leu Gly Ala Ile Arg Glu Asp Asn Asn Ile Thr
            195                 200                 205
Leu Lys Leu Asp Arg Cys Asn Asn Asn Asn Gln Tyr Val Ser Ile Asp
        210                 215                 220
Lys Phe Arg Ile Phe Cys Lys Ala Leu Asn Pro Lys Glu Ile Glu Lys
225                 230                 235                 240
Leu Tyr Thr Ser Tyr Leu Ser Ile Thr Phe Leu Arg Asp Phe Trp Gly
                245                 250                 255
Asn Pro Leu Arg Tyr Asp Thr Glu Tyr Tyr Leu Ile Pro Val Ala Ser
                260                 265                 270
Ser Ser Lys Asp Val Gln Leu Lys Asn Ile Thr Asp Tyr Met Tyr Leu
        275                 280                 285
Thr Asn Ala Pro Ser Tyr Thr Asn Gly Lys Leu Asn Ile Tyr Tyr Arg
    290                 295                 300
Arg Leu Tyr Asn Gly Leu Lys Phe Ile Ile Lys Arg Tyr Thr Pro Asn
305                 310                 315                 320
Asn Glu Ile Asp Ser Phe Val Lys Ser Gly Asp Phe Ile Lys Leu Tyr
                325                 330                 335
Val Ser Tyr Asn Asn Asn Glu His Ile Val Gly Tyr Pro Lys Asp Gly
```

340                              345                              350
Asn Ala Phe Asn Asn Leu Asp Arg Ile Leu Arg Val Gly Tyr Asn Ala
        355                     360                     365
Pro Gly Ile Pro Leu Tyr Lys Lys Met Glu Ala Val Lys Leu Arg Asp
    370                     375                     380
Leu Lys Thr Tyr Ser Val Gln Leu Lys Leu Tyr Asp Asp Lys Asn Ala
385                     390                     395                     400
Ser Leu Gly Leu Val Gly Thr His Asn Gly Gln Ile Gly Asn Asp Pro
                405                     410                     415
Asn Arg Asp Ile Leu Ile Ala Ser Asn Trp Tyr Phe Asn His Leu Lys
            420                     425                     430
Asp Lys Ile Leu Gly Cys Asp Trp Tyr Phe Val Pro Thr Asp Glu Gly
        435                     440                     445
Trp Thr Asn Asp
450

(2) INFORMATION FOR SEQ ID NO:3:

(i) SEQUENCE CHARACTERISTICS:
      (A) LENGTH: 1359 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vi) ORIGINAL SOURCE:
       (A) ORGANISM: Clostridium tetani (ix) FEATURE:
       (A) NAME/KEY: CDS
       (B) LOCATION: 1..1356

(xi) SEQUENCE DESCRIPTION: SEQ ID NO:3:

ATG AAA AAC CTT GAT TGT TGG GTC GAC AAC GAA GAA GAC ATC GAT GTT    48
Met Lys Asn Leu Asp Cys Trp Val Asp Asn Glu Glu Asp Ile Asp Val
1               5                   10                  15

ATC CTG AAA AAG TCT ACC ATT CTG AAC TTG GAC ATC AAC AAC GAT ATT    96
Ile Leu Lys Lys Ser Thr Ile Leu Asn Leu Asp Ile Asn Asn Asp Ile
            20                  25                  30

ATC TCC GAC ATC TCT GGT TTC AAC TCC TCT GTT ATC ACA TAT CCA GAT    144
Ile Ser Asp Ile Ser Gly Phe Asn Ser Ser Val Ile Thr Tyr Pro Asp
        35                  40                  45

GCT CAA TTG GTG CCG GGC ATC AAC GGC AAA GCT ATC CAC CTG GTT AAC    192
Ala Gln Leu Val Pro Gly Ile Asn Gly Lys Ala Ile His Leu Val Asn
    50                  55                  60

AAC GAA TCT TCT GAA GTT ATC GTG CAC AAG GCC ATG GAC ATC GAA TAC    240
Asn Glu Ser Ser Glu Val Ile Val His Lys Ala Met Asp Ile Glu Tyr
65                  70                  75                  80

AAC GAC ATG TTC AAC AAC TTC ACC GTT AGC TTC TGG CTG CGC GTT CCG    288
Asn Asp Met Phe Asn Asn Phe Thr Val Ser Phe Trp Leu Arg Val Pro
                85                  90                  95

AAA GTT TCT GCT TCC CAC CTG GAA CAG TAC GGC ACT AAC GAG TAC TCC    336
Lys Val Ser Ala Ser His Leu Glu Gln Tyr Gly Thr Asn Glu Tyr Ser
            100                 105                 110

ATC ATC AGC TCT ATG AAG AAA CAC TCC CTG TCC ATC GGC TCT GGT TGG    384
Ile Ile Ser Ser Met Lys Lys His Ser Leu Ser Ile Gly Ser Gly Trp
        115                 120                 125

TCT GTT TCC CTG AAG GGT AAC AAC CTG ATC TGG ACT CTG AAA GAC TCC    432
Ser Val Ser Leu Lys Gly Asn Asn Leu Ile Trp Thr Leu Lys Asp Ser
    130                 135                 140

| | | | | | | | | | | | | | | | | |
|---|---|---|---|---|---|---|---|---|---|---|---|---|---|---|---|---|
| GCG | GGC | GAA | GTT | CGT | CAG | ATC | ACT | TTC | CGC | GAC | CTG | CCG | GAC | AAG | TTC | 480 |
| Ala | Gly | Glu | Val | Arg | Gln | Ile | Thr | Phe | Arg | Asp | Leu | Pro | Asp | Lys | Phe | |
| 145 | | | | | 150 | | | | 155 | | | | | | 160 | |
| AAC | GCG | TAC | CTG | GCT | AAC | AAA | TGG | GTT | TTC | ATC | ACT | ATC | ACT | AAC | GAT | 528 |
| Asn | Ala | Tyr | Leu | Ala | Asn | Lys | Trp | Val | Phe | Ile | Thr | Ile | Thr | Asn | Asp | |
| | | | | | 165 | | | | 170 | | | | | 175 | | |
| CGT | CTG | TCT | TCT | GCT | AAC | CTG | TAC | ATC | AAC | GGC | GTT | CTG | ATG | GGC | TCC | 576 |
| Arg | Leu | Ser | Ser | Ala | Asn | Leu | Tyr | Ile | Asn | Gly | Val | Leu | Met | Gly | Ser | |
| | | | 180 | | | | | 185 | | | | | 190 | | | |
| GCT | GAA | ATC | ACT | GGT | CTG | GGC | GCT | ATC | CGT | GAG | GAC | AAC | AAC | ATC | ACT | 624 |
| Ala | Glu | Ile | Thr | Gly | Leu | Gly | Ala | Ile | Arg | Glu | Asp | Asn | Asn | Ile | Thr | |
| | | 195 | | | | | 200 | | | | | 205 | | | | |
| CTT | AAG | CTG | GAC | CGT | TGC | AAC | AAC | AAC | CAG | TAC | GTA | TCC | ATC | GAC | | 672 |
| Leu | Lys | Leu | Asp | Arg | Cys | Asn | Asn | Asn | Gln | Tyr | Val | Ser | Ile | Asp | | |
| 210 | | | | | 215 | | | | | 220 | | | | | | |
| AAG | TTC | CGT | ATC | TTC | TGC | AAA | GCA | CTG | AAC | CCG | AAA | GAG | ATC | GAA | AAA | 720 |
| Lys | Phe | Arg | Ile | Phe | Cys | Lys | Ala | Leu | Asn | Pro | Lys | Glu | Ile | Glu | Lys | |
| 225 | | | | | 230 | | | | | 235 | | | | | 240 | |
| CTG | TAT | ACC | AGC | TAC | CTG | TCT | ATC | ACC | TTC | CTG | CGT | GAC | TTC | TGG | GGT | 768 |
| Leu | Tyr | Thr | Ser | Tyr | Leu | Ser | Ile | Thr | Phe | Leu | Arg | Asp | Phe | Trp | Gly | |
| | | | | 245 | | | | | 250 | | | | | 255 | | |
| AAC | CCG | CTG | CGT | TAC | GAC | ACC | GAA | TAT | TAC | CTG | ATC | CCG | GTA | GCT | TCT | 816 |
| Asn | Pro | Leu | Arg | Tyr | Asp | Thr | Glu | Tyr | Tyr | Leu | Ile | Pro | Val | Ala | Ser | |
| | | | 260 | | | | | 265 | | | | | 270 | | | |
| AGC | TCT | AAA | GAC | GTT | CAG | CTG | AAA | AAC | ATC | ACT | GAC | TAC | ATG | TAC | CTG | 864 |
| Ser | Ser | Lys | Asp | Val | Gln | Leu | Lys | Asn | Ile | Thr | Asp | Tyr | Met | Tyr | Leu | |
| | | 275 | | | | | 280 | | | | | 285 | | | | |
| ACC | AAC | GCG | CCG | TCC | TAC | ACT | AAC | GGT | AAA | CTG | AAC | ATC | TAC | TAC | CGA | 912 |
| Thr | Asn | Ala | Pro | Ser | Tyr | Thr | Asn | Gly | Lys | Leu | Asn | Ile | Tyr | Tyr | Arg | |
| | 290 | | | | | 295 | | | | | 300 | | | | | |
| CGT | CTG | TAC | AAC | GGC | CTG | AAA | TTC | ATC | ATC | AAA | CGC | TAC | ACT | CCG | AAC | 960 |
| Arg | Leu | Tyr | Asn | Gly | Leu | Lys | Phe | Ile | Ile | Lys | Arg | Tyr | Thr | Pro | Asn | |
| 305 | | | | | 310 | | | | | 315 | | | | | 320 | |
| AAC | GAA | ATC | GAT | TCT | TTC | GTT | AAA | TCT | GGT | GAC | TTC | ATC | AAA | CTG | TAC | 1008 |
| Asn | Glu | Ile | Asp | Ser | Phe | Val | Lys | Ser | Gly | Asp | Phe | Ile | Lys | Leu | Tyr | |
| | | | | 325 | | | | | 330 | | | | | 335 | | |
| GTT | TCT | TAC | AAC | AAC | AAC | GAA | CAC | ATC | GTT | GGT | TAC | CCG | AAA | GAC | GGT | 1056 |
| Val | Ser | Tyr | Asn | Asn | Asn | Glu | His | Ile | Val | Gly | Tyr | Pro | Lys | Asp | Gly | |
| | | | 340 | | | | | 345 | | | | | 350 | | | |
| AAC | GCT | TTC | AAC | AAC | CTG | GAC | AGA | ATT | CTG | CGT | GTT | GGT | TAC | AAC | GCT | 1104 |
| Asn | Ala | Phe | Asn | Asn | Leu | Asp | Arg | Ile | Leu | Arg | Val | Gly | Tyr | Asn | Ala | |
| | | 355 | | | | | 360 | | | | | 365 | | | | |
| CCG | GGT | ATC | CCG | CTG | TAC | AAA | AAA | ATG | GAA | GCT | GTT | AAA | CTG | CGT | GAC | 1152 |
| Pro | Gly | Ile | Pro | Leu | Tyr | Lys | Lys | Met | Glu | Ala | Val | Lys | Leu | Arg | Asp | |
| | 370 | | | | | 375 | | | | | 380 | | | | | |
| CTG | AAA | ACC | TAC | TCT | GTT | CAG | CTG | AAA | CTG | TAC | GAC | GAC | AAA | AAC | GCT | 1200 |
| Leu | Lys | Thr | Tyr | Ser | Val | Gln | Leu | Lys | Leu | Tyr | Asp | Asp | Lys | Asn | Ala | |
| 385 | | | | | 390 | | | | | 395 | | | | | 400 | |
| TCT | CTG | GGT | CTG | GTT | GGT | ACC | CAC | AAC | GGT | CAG | ATC | GGT | AAC | GAC | CCG | 1248 |
| Ser | Leu | Gly | Leu | Val | Gly | Thr | His | Asn | Gly | Gln | Ile | Gly | Asn | Asp | Pro | |
| | | | | 405 | | | | | 410 | | | | | 415 | | |
| AAC | CGT | GAC | ATC | CTG | ATC | GCT | TCT | AAC | TGG | TAC | TTC | AAC | CAC | CTG | AAA | 1296 |
| Asn | Arg | Asp | Ile | Leu | Ile | Ala | Ser | Asn | Trp | Tyr | Phe | Asn | His | Leu | Lys | |
| | | | 420 | | | | | 425 | | | | | 430 | | | |
| GAC | AAA | ATC | CTG | GGT | TGC | GAC | TGG | TAC | TTC | GTT | CCG | ACC | GAT | GAA | GGT | 1344 |
| Asp | Lys | Ile | Leu | Gly | Cys | Asp | Trp | Tyr | Phe | Val | Pro | Thr | Asp | Glu | Gly | |
| | | 435 | | | | | 440 | | | | | 445 | | | | |
| TGG | ACC | AAC | GAC | TAA | | | | | | | | | | | | 1359 |
| Trp | Thr | Asn | Asp | | | | | | | | | | | | | |
| 450 | | | | | | | | | | | | | | | | |

(2) INFORMATION FOR SEQ ID NO:4:

(i) SEQUENCE CHARACTERISTICS:
        (A) LENGTH: 452 amino acids
        (B) TYPE: amino acid
        (D) TOPOLOGY: linear (ii) MOLECULE TYPE: protein (xi) SEQUENCE DESCRIPTION: SEQ ID NO:4:

```
Met Lys Asn Leu Asp Cys Trp Val Asp Asn Glu Glu Asp Ile Asp Val
 1               5                  10                  15
Ile Leu Lys Lys Ser Thr Ile Leu Asn Leu Asp Ile Asn Asn Asp Ile
            20                  25                  30
Ile Ser Asp Ile Ser Gly Phe Asn Ser Ser Val Ile Thr Tyr Pro Asp
        35                  40                  45
Ala Gln Leu Val Pro Gly Ile Asn Gly Lys Ala Ile His Leu Val Asn
    50                  55                  60
Asn Glu Ser Ser Glu Val Ile Val His Lys Ala Met Asp Ile Glu Tyr
65                  70                  75                  80
Asn Asp Met Phe Asn Asn Phe Thr Val Ser Phe Trp Leu Arg Val Pro
                85                  90                  95
Lys Val Ser Ala Ser His Leu Glu Gln Tyr Gly Thr Asn Glu Tyr Ser
            100                 105                 110
Ile Ile Ser Ser Met Lys Lys His Ser Leu Ser Ile Gly Ser Gly Trp
        115                 120                 125
  Ser Val Ser Leu Lys Gly Asn Asn Leu Ile Trp Thr Leu Lys Asp Ser
        130                 135                 140
Ala Gly Glu Val Arg Gln Ile Thr Phe Arg Asp Leu Pro Asp Lys Phe
145                 150                 155                 160
Asn Ala Tyr Leu Ala Asn Lys Trp Val Phe Ile Thr Ile Thr Asn Asp
                165                 170                 175
Arg Leu Ser Ser Ala Asn Leu Tyr Ile Asn Gly Val Leu Met Gly Ser
            180                 185                 190
Ala Glu Ile Thr Gly Leu Gly Ala Ile Arg Glu Asp Asn Asn Ile Thr
        195                 200                 205
Leu Lys Leu Asp Arg Cys Asn Asn Asn Asn Gln Tyr Val Ser Ile Asp
    210                 215                 220
Lys Phe Arg Ile Phe Cys Lys Ala Leu Asn Pro Lys Glu Ile Glu Lys
225                 230                 235                 240
Leu Tyr Thr Ser Tyr Leu Ser Ile Thr Phe Leu Arg Asp Phe Trp Gly
                245                 250                 255
Asn Pro Leu Arg Tyr Asp Thr Glu Tyr Tyr Leu Ile Pro Val Ala Ser
            260                 265                 270
Ser Ser Lys Asp Val Gln Leu Lys Asn Ile Thr Asp Tyr Met Tyr Leu
        275                 280                 285
Thr Asn Ala Pro Ser Tyr Thr Asn Gly Lys Leu Asn Ile Tyr Tyr Arg
    290                 295                 300
Arg Leu Tyr Asn Gly Leu Lys Phe Ile Ile Lys Arg Tyr Thr Pro Asn
305                 310                 315                 320
  Asn Glu Ile Asp Ser Phe Val Lys Ser Gly Asp Phe Ile Lys Leu Tyr
            325                 330                 335
Val Ser Tyr Asn Asn Asn Glu His Ile Val Gly Tyr Pro Lys Asp Gly
            340                 345                 350
Asn Ala Phe Asn Asn Leu Asp Arg Ile Leu Arg Val Gly Tyr Asn Ala
        355                 360                 365
Pro Gly Ile Pro Leu Tyr Lys Lys Met Glu Ala Val Lys Leu Arg Asp
370                 375                 380
```

| | | | | | | | | | | | | | | |
|---|---|---|---|---|---|---|---|---|---|---|---|---|---|---|
| Leu | Lys | Thr | Tyr | Ser | Val | Gln | Leu | Lys | Leu | Tyr | Asp | Asp | Lys | Asn | Ala |
| 385 | | | | | 390 | | | | | 395 | | | | | 400 |

| Ser | Leu | Gly | Leu | Val | Gly | Thr | His | Asn | Gly | Gln | Ile | Gly | Asn | Asp | Pro |
|---|---|---|---|---|---|---|---|---|---|---|---|---|---|---|---|
| | | | | 405 | | | | | 410 | | | | | 415 | |

| Asn | Arg | Asp | Ile | Leu | Ile | Ala | Ser | Asn | Trp | Tyr | Phe | Asn | His | Leu | Lys |
|---|---|---|---|---|---|---|---|---|---|---|---|---|---|---|---|
| | | | 420 | | | | | 425 | | | | | 430 | | |

| Asp | Lys | Ile | Leu | Gly | Cys | Asp | Trp | Tyr | Phe | Val | Pro | Thr | Asp | Glu | Gly |
|---|---|---|---|---|---|---|---|---|---|---|---|---|---|---|---|
| | | 435 | | | | | 440 | | | | | 445 | | | |

| Trp | Thr | Asn | Asp |
|---|---|---|---|
| 450 | | | |

( 2 ) INFORMATION FOR SEQ ID NO:5:

( i ) SEQUENCE CHARACTERISTICS:
        ( A ) LENGTH: 310 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Clostridium tetani ( x i ) SEQUENCE DESCRIPTION: SEQ ID NO:5:

```
CTCGAGACGT CTATACTTCG GAGCACTGTT GAGCGAAGGC TCATTAGATA TATTTTCTGT   60

CATTTTCCTT AACCCAAAAA TAAGGGAGAG GGTCCAAAAA GCGCTCGGAC AACTGTTGAC  120

CGTGATCCGA AGGACTGGCT ATACAGTGTT CACAAAATAG CCAAGCTGAA AATAATGTGT  180

AGCCTTTAGC TATGTTCAGT TAGTTTGGCT AGCAAAGATA TAAAAGCAGG TCGGAAATAT  240

TTATGGGCAT TATTATGCAG AGGATCCACA TGATAAAAAA AACAGTTGAA TATTCCCTCA  300

AAAATGACTG                                                        310
```

( 2 ) INFORMATION FOR SEQ ID NO:6:

( i ) SEQUENCE CHARACTERISTICS:
        ( A ) LENGTH: 32 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Synthetic ( i x ) FEATURE:
        ( A ) NAME/KEY: miscfeature
        ( B ) LOCATION: 1..4
        ( D ) OTHER INFORMATION: /function=sticky ends ( x i ) SEQUENCE DESCRIPTION: SEQ ID NO:6:

```
GATCTAAACG ATGAAAAACC TTGATTGTTG GG                                 32
```

( 2 ) INFORMATION FOR SEQ ID NO:7:

( i ) SEQUENCE CHARACTERISTICS:
        ( A ) LENGTH: 32 base pairs
        ( B ) TYPE: nucleic acid
        ( C ) STRANDEDNESS: double (D) TOPOLOGY: linear (ii) MOLECULE TYPE: DNA (genomic)

(vi) ORIGINAL SOURCE:
    (A) ORGANISM: synthetic (ix) FEATURE:
    (A) NAME/KEY: miscfeature
    (B) LOCATION: 1..4
    (D) OTHER INFORMATION: /function=sticky ends (xi) SEQUENCE DESCRIPTION: SEQ ID NO:7:

TCGACCCAAC AATCAAGGTT TTTCATCGTT TA　　　　　　　　　　　　　　　　32

(2) INFORMATION FOR SEQ ID NO:8:

(i) SEQUENCE CHARACTERISTICS:
        (A) LENGTH: 63 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: SYNTHETIC (ix) FEATURE:
        (A) NAME/KEY: miscfeature
        (B) LOCATION: 1..4
        (D) OTHER INFORMATION: /function="STICKY END"
                /product="LABEL"

(xi) SEQUENCE DESCRIPTION: SEQ ID NO:8:

GATCTACATG ATAAAAAAAA GAGTTGAATA TTCCCTCAAC CATGGTTAAC TTGGACTGTT　　60

GGG　　　　　　　　　　　　　　　　　　　　　　　　　　　　　　　　　　　　　　　　　63

(2) INFORMATION FOR SEQ ID NO:9:

(i) SEQUENCE CHARACTERISTICS:
        (A) LENGTH: 63 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: SYNTHETIC (ix) FEATURE:
        (A) NAME/KEY: miscfeature
        (B) LOCATION: 1..4

(xi) SEQUENCE DESCRIPTION: SEQ ID NO:9:

TCGACCCAAC AGTCCAAGTT AACCATGGTT GAGGGAATAT TCAACTGTTT TTTTATCAT　　60

GTA　　　　　　　　　　　　　　　　　　　　　　　　　　　　　　　　　　　　　　　　　63

(2) INFORMATION FOR SEQ ID NO:10:

(i) SEQUENCE CHARACTERISTICS:
        (A) LENGTH: 312 base pairs
        (B) TYPE: nucleic acid
        (C) STRANDEDNESS: double
        (D) TOPOLOGY: linear (i i) MOLECULE TYPE: DNA (genomic)

(v i) ORIGINAL SOURCE:
  (A) ORGANISM: synthetic (i x) FEATURE:
  (A) NAME/KEY: CDS
  (B) LOCATION: 42..311

(x i) SEQUENCE DESCRIPTION: SEQ ID NO:10:

```
GATCTACATG ATAAAAAAAA CAGTTGAATA TTCCCTCAAA A ATG AGA TTT CCT       53
                                                Met Arg Phe Pro
                                                 1

TCA ATT TTT ACT GCA GTT TTA TTC GCA GCA TCC TCC GCA TTA GCT GCT    101
Ser Ile Phe Thr Ala Val Leu Phe Ala Ala Ser Ser Ala Leu Ala Ala
 5              10                  15                      20

CCA GTC AAC ACT ACA ACA GAA GAT GAA ACG GCA CAA ATT CCG GCT GAA    149
Pro Val Asn Thr Thr Thr Glu Asp Glu Thr Ala Gln Ile Pro Ala Glu
                25                  30                  35

GCT GTC ATC GGT TAC TCA GAT TTA GAA GGG GAT TTC GAT GTT GCT GTT    197
Ala Val Ile Gly Tyr Ser Asp Leu Glu Gly Asp Phe Asp Val Ala Val
            40                  45                  50

TTG CCA TTT TCC AAC AGC ACA AAT AAC GGG TTA TTG TTT ATA AAT ACT    245
Leu Pro Phe Ser Asn Ser Thr Asn Asn Gly Leu Leu Phe Ile Asn Thr
        55                  60                  65

ACT ATT GCC AGC ATT GCT GCT AAA GAA GAA GGG GTA TCT CTC GAG AAA    293
Thr Ile Ala Ser Ile Ala Ala Lys Glu Glu Gly Val Ser Leu Glu Lys
    70                  75                  80

AGA GAG GCT GAA GCC ATG G                                          312
Arg Glu Ala Glu Ala Met
 85              90
```

(2) INFORMATION FOR SEQ ID NO:11:

(i) SEQUENCE CHARACTERISTICS:
    (A) LENGTH: 90 amino acids
    (B) TYPE: amino acid
    (D) TOPOLOGY: linear (i i) MOLECULE TYPE: protein (x i) SEQUENCE DESCRIPTION: SEQ ID NO:11:

```
Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
 65                 70                  75                  80

Ser Leu Glu Lys Arg Glu Ala Glu Ala Met
                85                  90
```

(2) INFORMATION FOR SEQ ID NO:12:

(i) SEQUENCE CHARACTERISTICS:
    (A) LENGTH: 75 base pairs
    (B) TYPE: nucleic acid
    (C) STRANDEDNESS: double
    (D) TOPOLOGY: linear (i i) MOLECULE TYPE: DNA (genomic)

-continued (vi) ORIGINAL SOURCE:
  (A) ORGANISM: synthetic (ix) FEATURE:
  (A) NAME/KEY: miscfeature
  (B) LOCATION: 1..2

(xi) SEQUENCE DESCRIPTION: SEQ ID NO:12:

CGAAGGATCC AAACGATGAG ATTTCCTTCA ATTTTTACTG CAGACTAGTC CCGGGTAAGT 60

AAGTAAGCGG CCGCG 75

(2) INFORMATION FOR SEQ ID NO:13:

(i) SEQUENCE CHARACTERISTICS:
    (A) LENGTH: 77 base pairs
    (B) TYPE: nucleic acid
    (C) STRANDEDNESS: double
    (D) TOPOLOGY: linear (ii) MOLECULE TYPE: DNA (genomic)

(vi) ORIGINAL SOURCE:
    (A) ORGANISM: synthetic (ix) FEATURE:
    (A) NAME/KEY: miscfeature
    (B) LOCATION: 1..4

(xi) SEQUENCE DESCRIPTION: SEQ ID NO:13:

AATTCGCGGC CGCTTACTTA CTTACCCGGG ACTAGTCTGC AGTAAAAATT GAAGGAAATC 60

TCATCGTTTG GATCCTT 77

EXPRESSION OF TETANUS TOXIN FRAGMENT C IN YEAST

The present invention relates to the production of tetanus toxin C fragment.

Vaccination against tetanus is effective in the prevention of this disease in most Western countries, although incomplete vaccination in some third world countries can account for up to one million cases of tetanus every year. Current tetanus vaccines are produced by formaldehyde treatment of tetanus toxin produced by the anaerobic bacterium *C. tetani* to produce the immunogenic toxoid. It has been suggested that impurities incorporated during formaldehyde treatment are partly responsible for the adverse effects sometimes seen with hyperimmunisation with tetanus toxoid.

The structural gene for tetanus toxin has been cloned and sequenced (Fairweather, N. F., et al, J. Bacteriol. 165, 21–27 (1986); Fairweather, N. F., and Lyness, V. A., Nuc. Acid Res. 14, 7809–7812 (1986). These studies have confirmed the structure of tetanus toxin as a 150kD protein of 1315 amino acids. The toxin can be cleaved by various treatments into several fragments. Fragment C, comprising the C terminal 451 amino acids, is a 50kD polypeptide generated by papain cleavage of toxin.

Fragment C derived in this way has been shown to be non-toxic and is capable of immunising mice and guinea pigs (Helting, T. B., and Zwisler, O., J. Biol. Chem. 252, 187–193 (1977); Helting, T. B., and Nau, H. H., Act. Pathol. Microbiol. Scan. Sect. C 92, 59–63 (1984)). Papain digestion also releases the 100 kD fragment B, comprising the N-terminal part of the toxin molecule. Fragment B is also protective, but has been reported to be toxic to animals at high doses (Helting, T. B., et al, J. Biol. Chem. 253,125–125, (1978)).

Portions of tetanus toxin containing fragment C have been expressed in *E.coli* (Fairweather, N. F., et al, J. Bacteriol, 165, 21–27, (1986));

Fairweather, N. F., et al, Infection and Immunity 55, 2541-2545, (1987); EP-A-0209281). These portions of tetanus toxin which were expressed were either fused to part of the *E.coli* trpE protein or comprised part of fragment B and all of fragment C of tetanus toxin. All the above were found to be expressed at low levels and were all insoluble in the cytoplasm of *E.coli* cells.

It has been found previously that when fragment C on its own is expressed in *E.coli*, it is soluble in the cytoplasm of the cells. Fragment C was expressed using two plasmids, pTETtac1 and pTETtac2 which were derived from the high expressing plasmid pIFGtac124A (Makoff, A. J., et al., Biochem. Soc. Trans., 16, 48–49, (1988)) Most of the coding sequence of pTETtac1 was provided by two restriction fragments. The rest of the sequence was encoded by a pair of synthetic oligonucleotides both 42 base pairs long, where the codon bias was optimised for expression in *E.coli*. Plasmid pTETtac2 was constructed from pTETtac1 by replacing the BglIIoSfa NI region by a pair of synthetic oligonucleotides (each 161 nucleotides long) which reproduced the sequence upstream of the initiation codon and optimised the coding sequence, at the beginning of the C fragment region, for expression in *E.coli* (Makoff, A. J., et al. Bio/Technology 7, 1043–1046 (1989)).

However, *E.coli* has the disadvantage as a host organism that it contains toxic pyrogenic factors (lipopolysaccharides from the cell wall) which must be rigorously excluded from the final product. The ease with which these factors may be excluded will depend on the protein product in question and the method by which it is purified from the cell. However, it would be preferable to eliminate the possibility of contamination altogether simply by using a non-toxic organism as the host, such as yeast.

In using the native sequence encoding fragment C, the inventors were unable to obtain expression in yeast and found that the barrier to expression was due to the fact that the mRNA transcripts of the gene were incomplete. Synthesis of the complete transcript probably involves at the 3'-end three closely linked steps: termination of the primary transcript, endonucleolytic processing and polyadenylation. (Platt, J.,Ann. Rev. Biochem., 55, 339–372, (1986)). The inventors have now identified the position of several "terminators" (termination/endo- nucleolytic processing/polyadenylation sites) present in the DNA. As a result the inventors were able to eliminate these and obtain successful expression in yeast of tetanus toxin fragment C.

FIG. 1 shows the position of at least six elements which are completely or partially responsible for the production of incomplete mRNA transcripts. The yeast terminator is poorly defined. Several different consensus sequences have been proposed (Henikoff, S., et al., Cell, 33, 607–614, (1983); Zaret, K. S., and Sherman, F., Cell, 28, 563–573, (1982); Bennetzen, J. L., and Hall, B. D., J.Biol. Chem., 257, 3018–3025, (1982a)), but it appears that there may be deviation from these sequences and it appears that other, undefined elements may also be necessary for termination (Osborne, B. I., and Guarente L., PNAS, 86, 4097–4101, (1989)). Yeast terminators occur in stretches of (A+T)-rich DNA, though not all (A+T)-rich DNA contains terminators. Our surprising finding was that the original fragment C DNA contained at least six elements which were responsible for incomplete transcription of the mRNA. The elements were eliminated by increasing the (G+C)-content at these positions thus providing for the production of a substantially complete mRNA transcript.

The present invention provides a novel DNA sequence encoding tetanus toxin fragment C and having a (G+C)-content that has been increased relative to the wild-type DNA sequence so as to allow the production of complete mRNA transcripts in yeast.

Tetanus toxin fragment C, as used herein, is defined as the wild type polypeptide having the amino acid sequence set forth in FIG. 2 and in Seq ID Nos: 1 and 2 or is a mutant polypeptide having an amino acid sequence that is at least 90% homologous with that set forth in FIG. 2 and that retains substantially the same biological and immunogenic properties as the wild-type polypeptide.

The amino acid sequence of fragment C may be varied by one or more amino acid substitutions, extensions, insertions and/or deletions provided the resulting polypeptide retains substantially the same biological and immunogenic properties as wild-type fragment C.

In the case of amino acid substitutions, one or more of the amino acid residues of fragment C may be replaced by one or more other amino acid residues which achieve this aim. Candidate substitutions include Ser for Thr and vice versa, Glu for Asp and vice versa, Gln for Asn and vice versa, Leu for Ile and vice versa, Ala for Val and vice versa and Arg for Lys and vice versa.

Mutant fragment C may be obtained by introducing nucleotide changes into the DNA sequence encoding wild-type fragment C, for example into the DNA sequence of FIG. 2 and SEQ ID No: 1. This may be achieved by any appropriate technique, including restriction of the sequence with an endonuclease, insertion of oligonucleotide linkers, use of an exonuclease and/or a polymerase and site-directed mutagenesis.

Fragment C wild-type DNA has a (G+C) - content of 29%, while the preferred DNA sequence in accordance with the present invention (see FIG. 2 and SEQ ID NO: 3) has 47%. The maximum possible (G+C) - content that can encode fragment C is 60%. A level of 40–60% (G+C)- content would thus allow the production of a complete mRNA transcript provided that were no localised concentrations of (A+T) rich DNA.

In designing a fragment C gene for expression in yeast, one route would be to use codons found in highly expressed yeast genes (Bennetzen, J. L., and Hall, B. D., J.Biol. Chem., 257, 3026–3031, (1982)) This would increase the (G+C)-content. Another important consideration would be to eliminate runs of (A+T) since these would raise the local (A+T)-content and might be sufficient to cause termination.

Since the elements responsible for the production of incomplete transcripts are only likely to extend over approximately 100 nucleotides, it is possible to achieve the same result by only increasing the (G+C)-content within these small regions.

Six regions were identified as being responsible for the incomplete production of mRNA transcripts by analysis of a number of different mutant DNA sequences containing differing lengths of DNA for which the (G+C)-content had been increased.

TABLE 1

| Region responsible for production of incomplete transcript in *C. tetani* DNA (nucleotides into coding sequence) | Region to be altered so as to allow the production of complete mRNA transcripts |
|---|---|
| 1. 560 ± 50 | 410–610 |
| 2. 660 ± 50 | 510–710 |
| 3. 800 ± 50 | 650–850 |
| 4. 1000 ± 100 | 800–1100 |
| 5. 1100 ± 100 | 900–1200 |
| 6. 1300 ± 100 | 1100–1400 |

It is believed that some of the regions are more responsible than others for the production of incomplete transcripts. It appears that regions 2 and 4 are most important. In order to allow the production of complete mRNA transcripts which is being prevented by regions 2 and 4 the (G+C)-content of mutant fragment DNA is increased relative to the native DNA sequence from nucleotide 510 to nucleotide 700 and from nucleotide 800 to nucleotide 1100, the numbers corresponding to those set forth in the sequence of FIG. 2 and in SEQ ID Nos: 1 and 3. The next most important regions are 3,5 and 6. Similarly, in order to allow the production of complete mRNA transcripts which are additionally being prevented by regions 3, 5 and 6 the (G+C)-content is additionally increased from nucleotide 650 to nucleotide 850, from nucleotide 900 to nucleotide 1200 and from nucleotide 1100 to nucleotide 1400, the numbers corresponding to those set forth in the sequence of FIG. 2. Region 1 may be too weak to interfere with the production of complete mRNA transcripts; however, in order to allow complete mRNA production which is being prevented by Region 1 the (G+C)-content is additionally increased from nucleotide 410 to nucleotide 610, the numbers corresponding to those set forth in the sequence of FIG. 2.

It can be seen from Table 1 that because of the clustering of elements, it is advisable to increase the (G+C)-content from nucleotide 410 to the 3'- end nucleotide, the numbers corresponding to those set forth in the sequence of FIG. 2 so as to allow the production of complete mRNA transcripts.

The novel DNA sequence according to the invention may be chemically synthesised and cloned using methodologies well-known in the art.

The novel DNA may then be cloned into a suitable vector and used to transform yeast which is then capable of expressing the polypeptide which is encoded by the novel DNA.

The vector may be any appropriate vector which is suitable for the cloning of the DNA and which may be used to transform a yeast cell and thereby express the relevant protein. Such vectors include autonomously replicating plasmids and chromosomal integration vectors.

Vectors which may be used for cloning DNA include pWYG7 (see Example 1 and FIG. 3), pWYG5 (see Example 2 and FIG. 5) and PIC3 (Example 6) for use in yeast.

In yet another feature of the present invention there is provided an expression vector, which incorporates a DNA sequence according to the invention and which is capable of expressing fragment C in yeast (See Examples 4 and 5).

The expression vector incorporates control elements for transcriptional initiation (promoters) and termination. The coding sequence of the gene to be expressed along with its own translational start and stop codons is inserted between these control elements.

Examples of promoters for use with the expression vector of the present invention include GAL1, GAL7, ADH2, PGK, GAPDH, etc. (Kingsman, S. M. et al., Biotechnology & Genetic Engineering Reviews, Vol. 3, 377–416, (1985); Russell, D. W. et al., The Journal of Biological Chemistry, Vol 258, No.4, 2674–2682 (1983)); and AOX1 (Digam, et al., Dev. Ind. Micro. Biol, 29, 59–65, (MS8)). Use of the inducible promoter such as the GAL1, GAL7 or ADH2 promoter may be preferred as it enables expression to be controlled. Expression of the GAL1 and GAL7 promoters is induced by galactose.

An appropriate expression vector may be obtained by cloning a DNA sequence according to the present invention into an expression vector. An example of a complete expression vector, containing the GAL1 promoter, is pWYG5-TET15 which contains the whole synthesised DNA encoding fragment C (see FIG. 12).

In a further aspect of the invention there is provided a yeast organism transformed with an expression vector according to the invention.

Examples of suitable host cells for use in the above-described method are yeast cells such as Saccharomyces, Pichia, Kluyveromyces or Hansenula and in particular the following species; *Saccharomyces cerevisiae, Kluyveromyces lactis, Hansenula polymorpha*, or *Pichia pastoris*.

A strain of yeast which can be used is *Saccharomyces cerevisiae* strain S150-2B.

The present invention provides a process for the preparation of fragment C of tetanus toxin which process comprises the steps of:

(i) preparing the DNA of fragment C to contain codons of increased (G+C)-content by chemically synthesising the entire coding sequence
(ii) inserting the DNA into a suitable vector
(iii) transforming yeast cells
(iv) culturing a transformed host to express fragment C of tetanus toxin
(v) recovering the product fragment C thus expressed Recombinant tetanus toxin fragment C may therefore be obtained thus facilitating its use as the basis for an alternative vaccine to formaldehyde treated tetanus toxoid and tetanus toxin fragment C as expressed in E.coli.

Step (iv) of the process of the invention comprises culturing yeast transformed by the expression vector of the present invention such as to cause expression of fragment C. Fragment C may then be isolated from the yeast cells by for example breaking the yeast cells with glass beads or when the material is secreted by isolation from the culture medium.

The DNA sequence and corresponding amino acid sequence encoded by plasmid pWYG5-TET15 mentioned below is shown in FIG. 2 and in SEQ ID Nos: 3 and 4. The symbol ,,, is shown under the translational stop codon. The nucleotide changes made in the synthesised gene are shown below the original C.tetani DNA sequence.

The fragment C that is expressed is recovered, in step (v) of the present process, from the yeast cells by similar protocols by standard purification procedures. (Makoff, A. J., et al., Bio/Technology, 7, 1043–1046, (1989a)).

The fragment C may be isolated to the desired degree of purity. Some minor yeast contaminants may also be present. Generally the degree of purity is at least 80%, preferably at least 90% and more preferably at least 95%.

The present invention also provides a vaccine for conferring immunity to tetanus comprising tetanus toxin fragment C prepared according to the invention and a pharmaceutically acceptable carrier or diluent. The vaccine may include other antigens to provide a multi-valent vaccine. Typically carriers and diluents are sterile, pyrogen-free liquid media suitable as vehicles for introducing a polypeptide into a patient. Isotonic saline solution may be employed.

The vaccine may also comprise an adjuvant for stimulating the immune response and thereby enhancing the effect of the vaccine. A convenient adjuvant is aluminium hydroxide. Conveniently the vaccines are formulated to contain a final concentration of fragment C or its derivative of from 0.2 to 200 $\mu$g/ml, preferably 5 to 50 $\mu$g/ml, most preferably about 30$\mu$g/ml. After formulation the vaccine may be incorporated into a sterile container which is then sealed and stored at a low temperature, for example 4° C., or it may be freeze-dried.

The vaccine may be administered by any conventional method for the administration of vaccines such as parenteral (e.g. subcutaneous or intramuscular) injection. The treatment may consist of a single dose of vaccine or a plurality of doses over a period of time. It is recommended that each dose is 0.1 to 2ml preferably 0.2 to 1 ml, most preferably about 0.5ml of vaccine.

The inventors have surprisingly found that it is possible to secrete fragment C into the culture medium using an appropriate secretion signal such as the alpha factor leader peptide. The protein was found to be secreted to a level of 5–10mg/l into the medium and was present in two forms in roughly equal amounts: a high molecular mass hyper-glycosylated protein (75–200kDa), and a core-glycosylated protein (65kDa). This glycosylated protein was found to be substantially inactive in vaccinating mice against tetanus toxin. However, if the glycosylated protein is de-glycosylated it becomes as active as the intracellular fragment C in immunising against tetanus.

As it should be possible to secrete fragment C to levels in excess of 100mg/l in high-density fermentations the de-glycosylated secreted product may provide a feasible production alternative to the intracellular protein production.

The invention will be described in more detail hereinafter with reference to the accompanying drawings in which:

FIG. 1 shows the location of elements responsible for the production of incomplete transcripts identified in the four variants of fragment C DNA having different amounts of synthesised DNA. Coding regions for fragment C are boxed; regions that were chemically synthesised with codons optimal for translation in E.coli are hatched. The four versions of the gene, TET2, TET7, TET11 and TET15, had 12%, 50%, 73% and 99% synthetic DNA, respectively. The approximate positions of yeast polyadenylation sites found in the native sequence, estimated from the sizes of short transcripts in Northern blots, are indicated by arrows. (The 5' synthesised region in TET2 extends 16Ont into the gene, and the first terminator is at 560±5Ont).

FIG. 2 shows the sequence of C.tetant DNA encoding fragment C (top line), the nucleotide changes made in the fully synthesised version of fragment C (middle line) and the amino acid sequence (third line) (SEQ. ID Nos: 1 to 4).

FIG. 4 shows the nucleotide sequence of the promoter region of GAL7 (SEQ ID No: 5). The synthesised promoter corresponds to the XhoI to BamHI fragment. Regions downstream of BamH1 are present in native GAL7 including the RNA start site ( ↓ ) and the initiating ATG (underlined). The two basepairs which were altered to give a BamHI site are underlined.

Figure 5A:
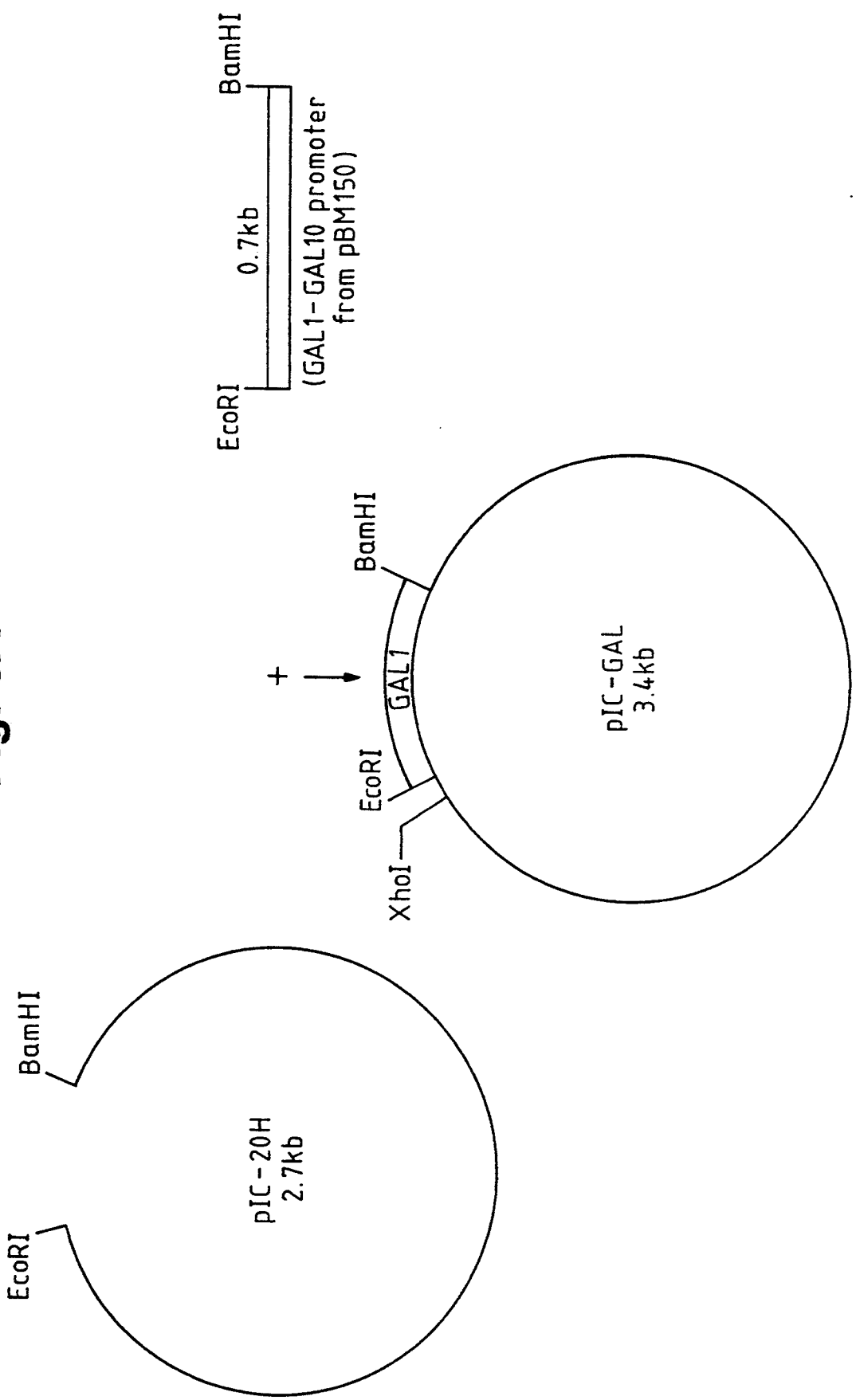

FIGS. 5 (i)-5(ii) shows the construction of yeast expression vector pWYG5.

Figure 6:
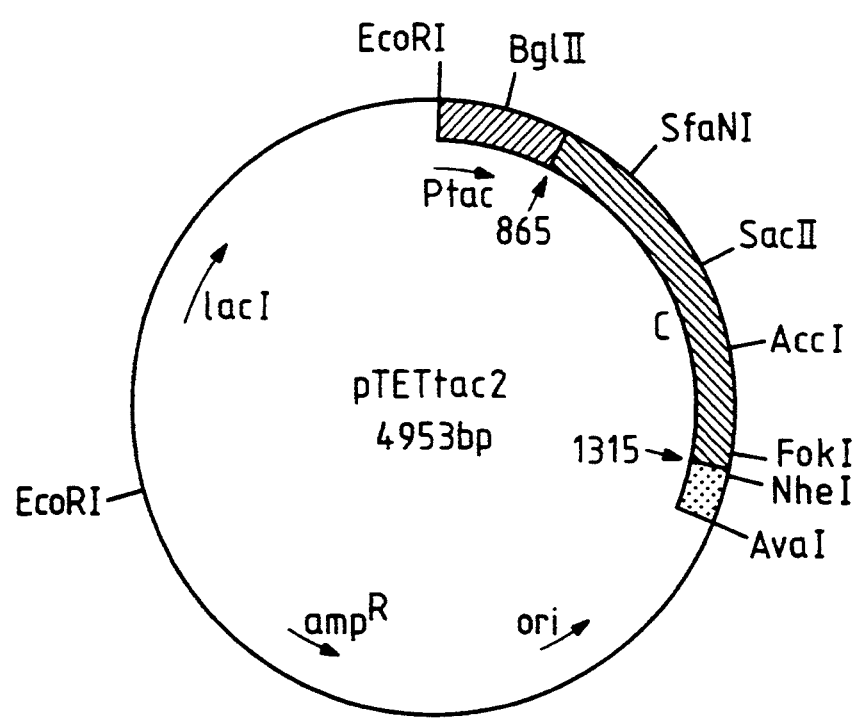

FIG. 6 shows the map of pTETtac2

Figure 7:
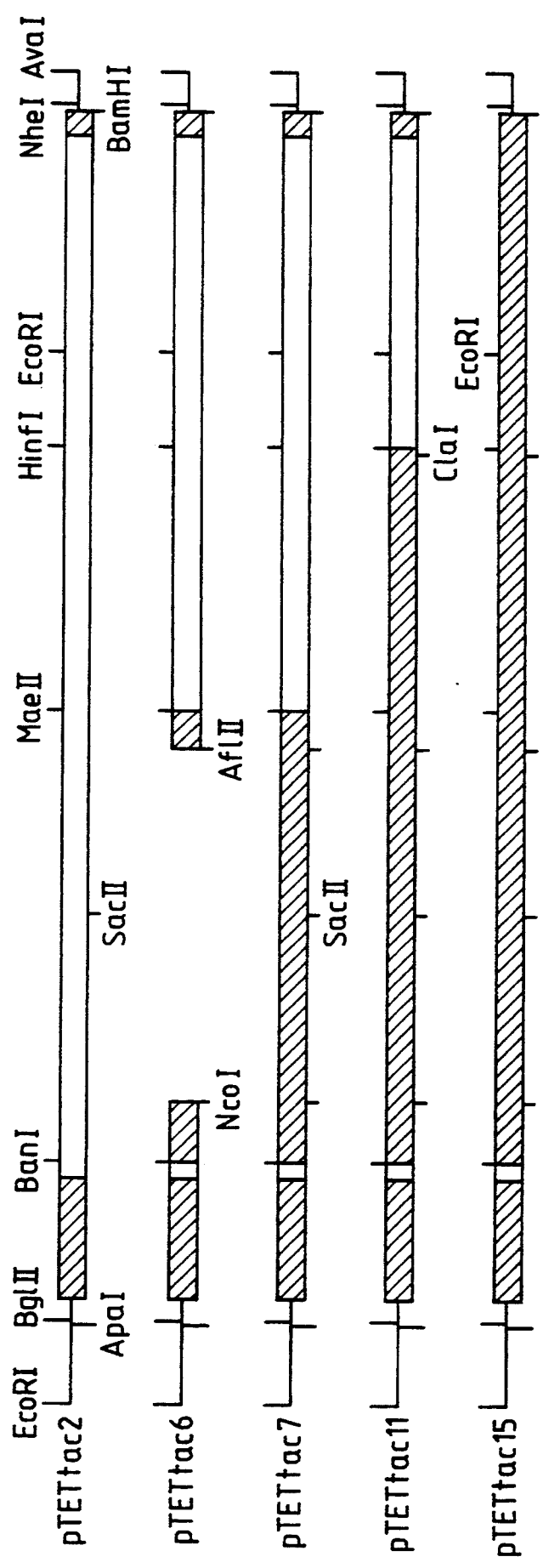

FIG. 7 shows the E.coli vector for expression of tetanus toxin fragment C (pTETtac2) with progressively more synthesised DNA containing optimal codons. Only the region between the EcoRI and AvaI sites is shown, the full map of pTETtac2 being given in FIG. 6. The fragment C coding regions are boxed and synthesised regions are hatched.

Figure 8B:
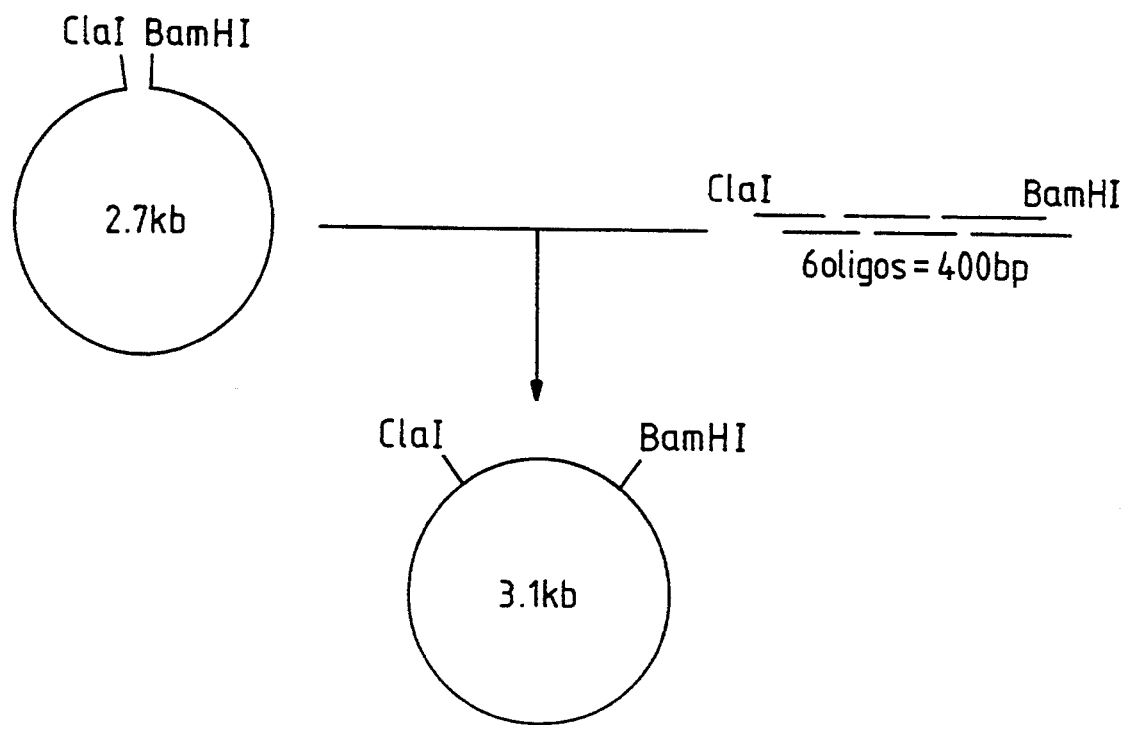
Figure 8C:
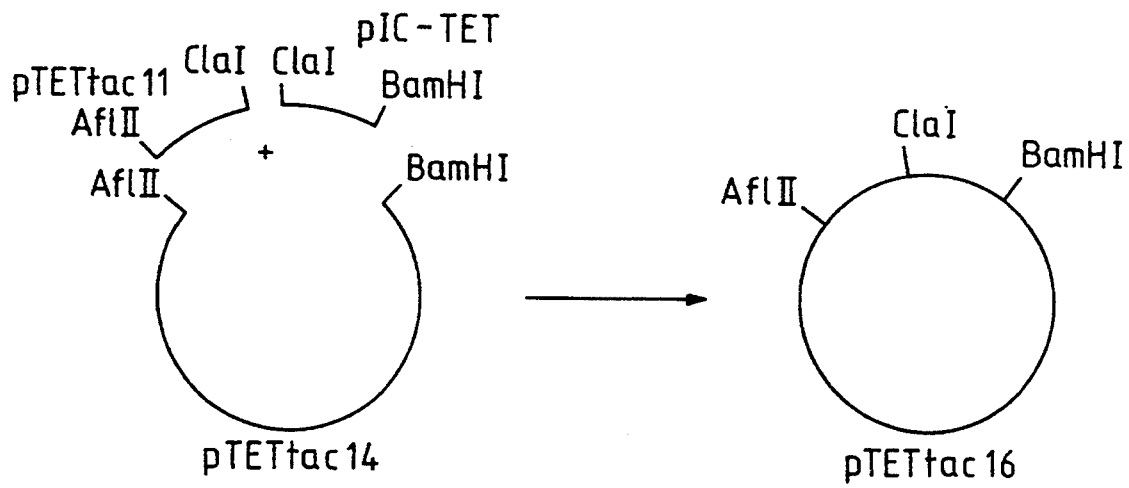
Figure 9A:
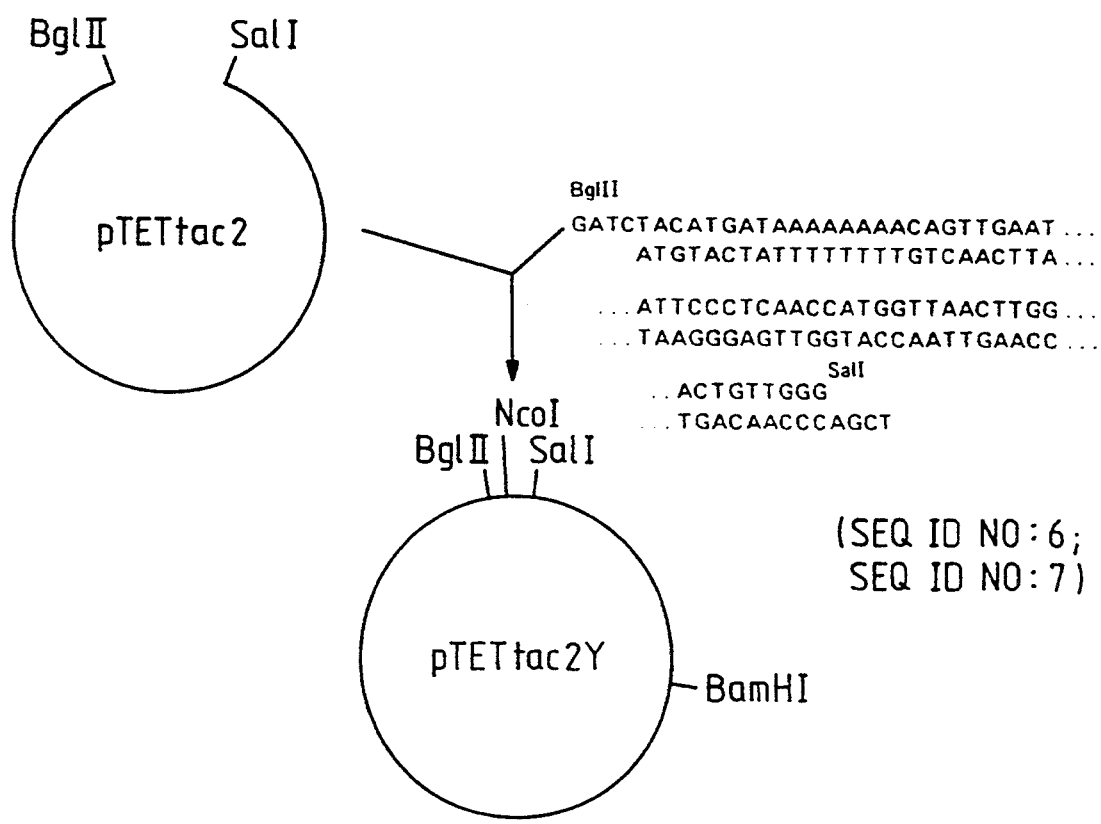

FIG. 8(i)-8(iii) shows the construction of pTETtac16. The oligonucleotides inserted into pTETtac7 to obtain pTETtac14 are shown in SEQ ID NOS: 6 and 7. FIG. 9i)-9(ii) shows the construction of pWYG7-TET2. The oligonucleotides inserted into pTETtac2 to obtain pTETtac2Y are shown in SEQ ID NOS: 8 and 9.

Figure 10:
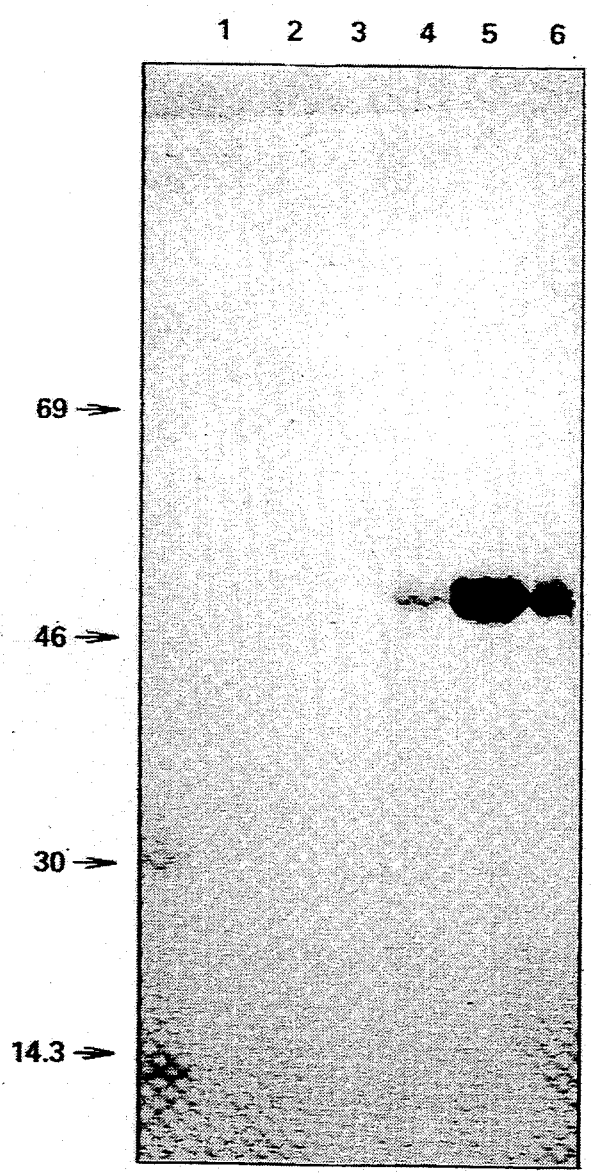

FIG. 10 shows a Western blot analysis of proteins from induced cells containing no plasmid, pWYG7-TET2, pWYG5-TET7, pWYG5-TET11 or pWYG5-TET15 (tracks 1 to 5, respectively). Track 6 was loaded with Met-fragment C produced in E coli. The proteins (50$\mu$g) were separated in a 9% SDS-polyacrylamide gel, blotted onto nitrocellulose, and probed with a rabbit anti-fragment C serum as first antibody. Track 3 contains a very faint doublet at about 30kDa which is not visible in the reproduction.

Figure 11:
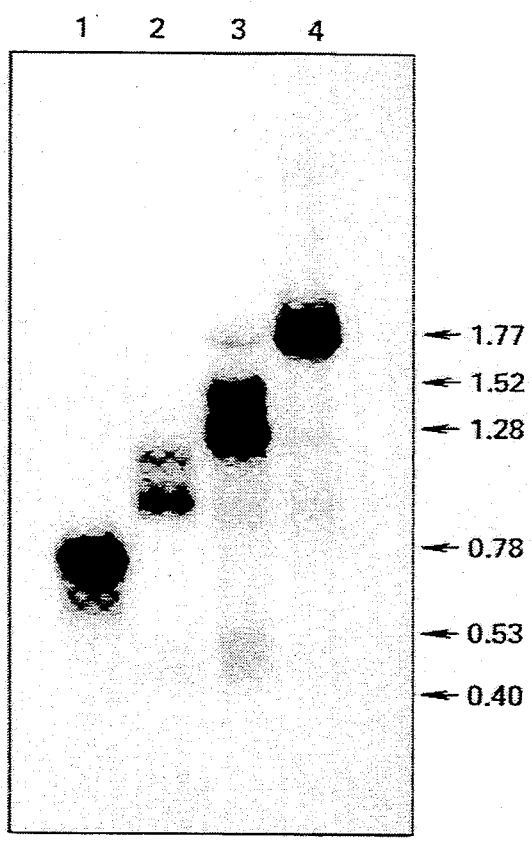

FIG. 11 shows a Northern blot of RNA extracted from induced cells transformed with pWYG7-TET2, pWYG5-TET7, pWYG5-TET11 and pWYG5-TET15 (tracks 1 to 4, respectively). The position of stained RNA size markers (size in kb) is indicated. The blot was probed with $^{32}$P-labelled 1.4kb BglII-BamHI fragment of pTETtac2.

Figure 12:
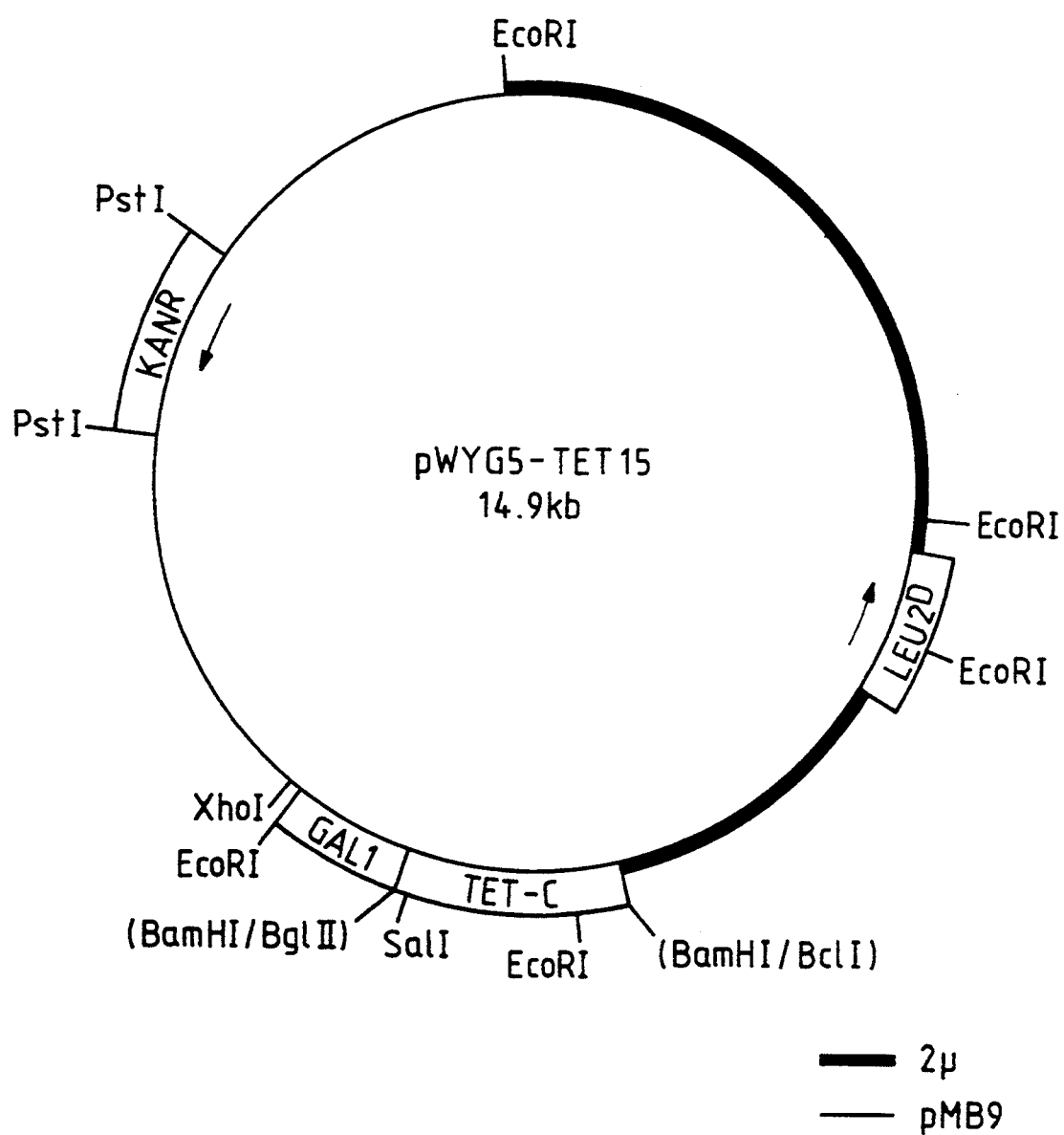

FIG. 12 shows the map of pWYG5-TET15

Figure 13:
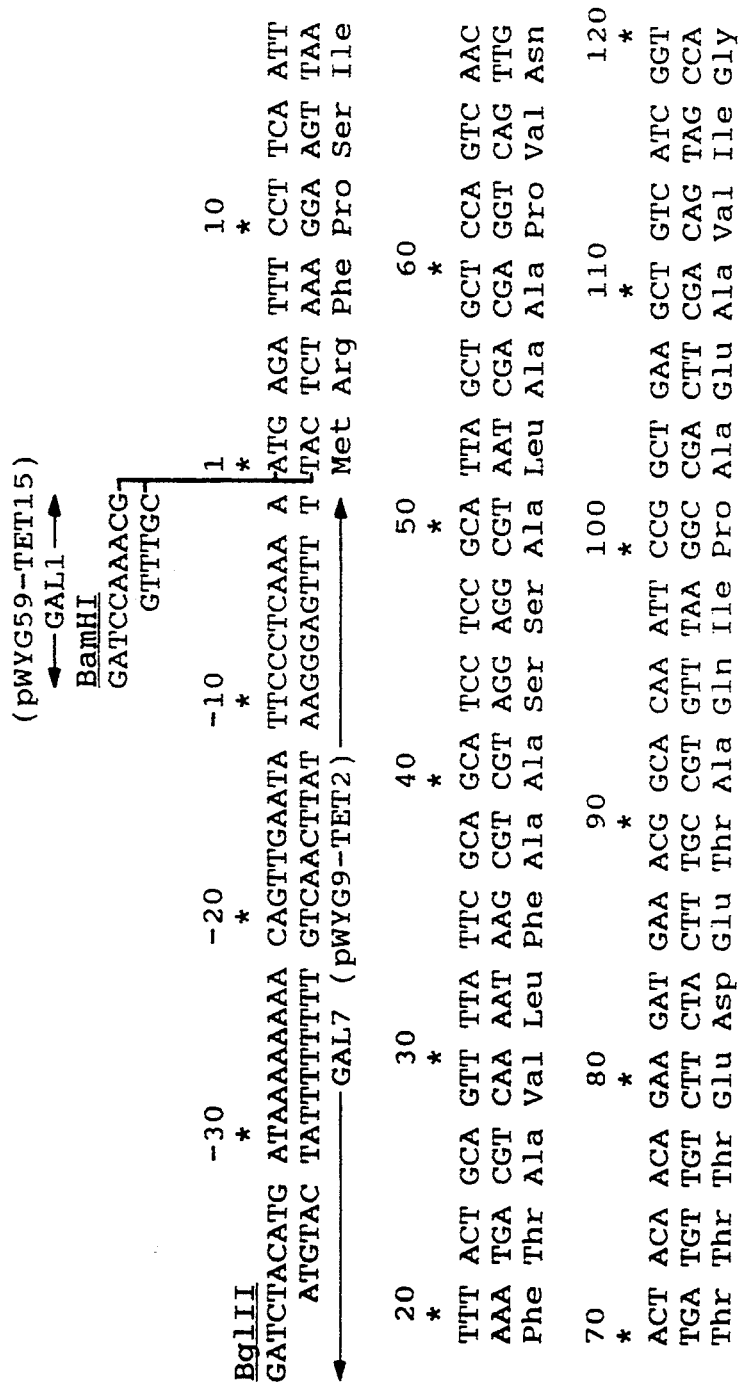

FIG. 13 shows the nucleotide sequence of the synthetic DNA fragments carrying the α-factor prepro region used in pWYG69-TET2 and pWYG59-TET15 (SEQ ID NOS: 10 and 11).

Figure 14:
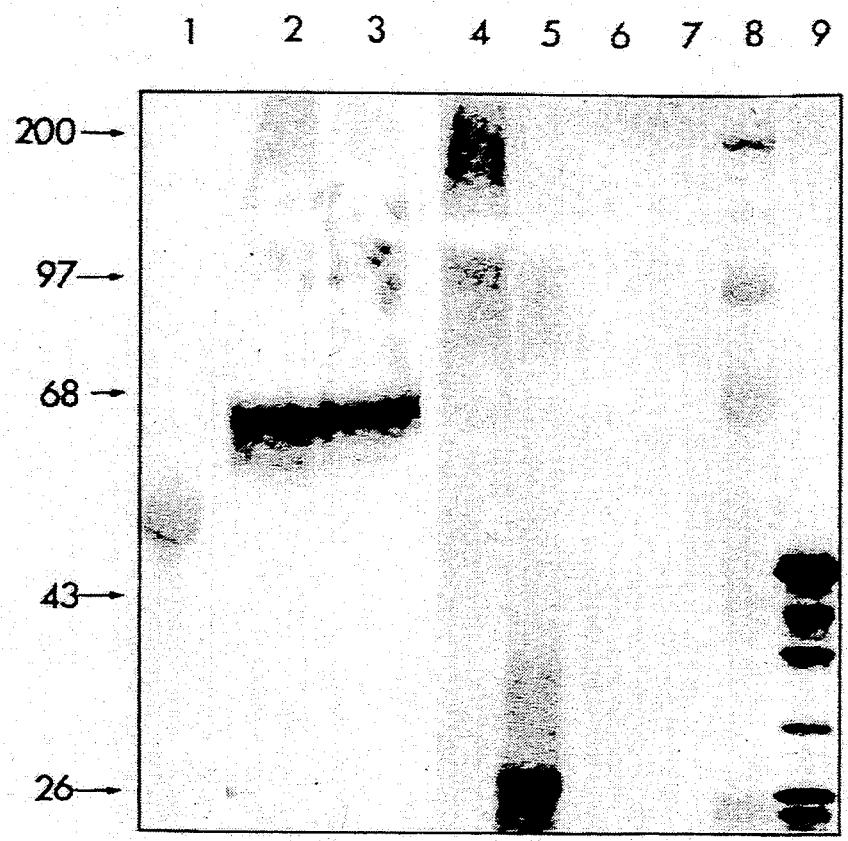

FIG. 14 shows a Western blot of secreted yeast fragment C. Lane 1, pWY659-TET15 culture supernatant treated with endoglycosidase H. Lanes 2 and 3, untreated pWY659-TET15 culture supernatant. Lane 4, pWYG9-TET2 culture supernatant. Lane 5, pWY69-TET2 culture supernatant treated with endoglycosidase H. Lane 6, culture supernatant from untransformed cells. Lane 7, culture supernatant from untransformed cells after endoglycosidase H treatment. Lane 8, molecular weight markers. Lane 9, fragment C produced in E.coli.

Figure 15A:
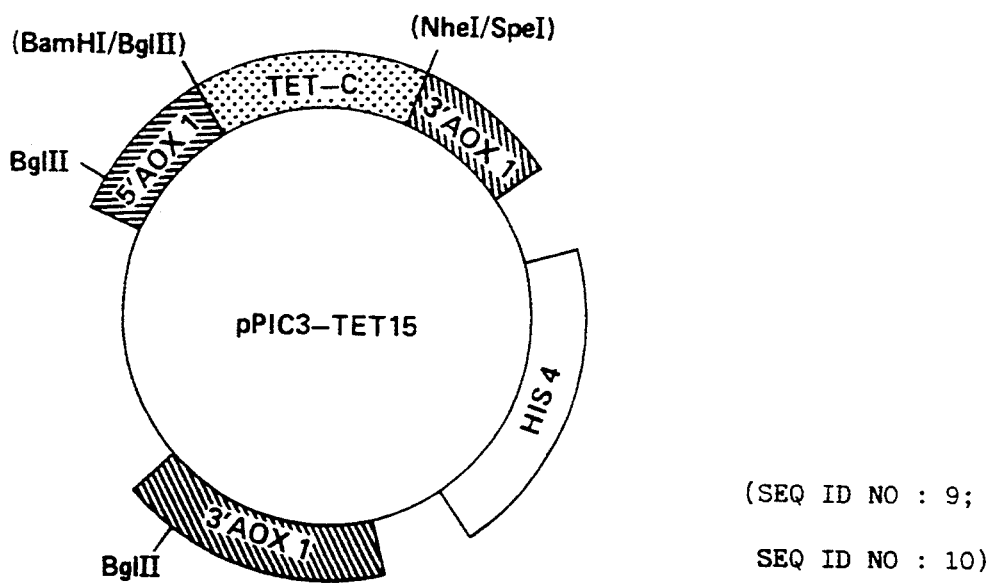
Figure 15B:
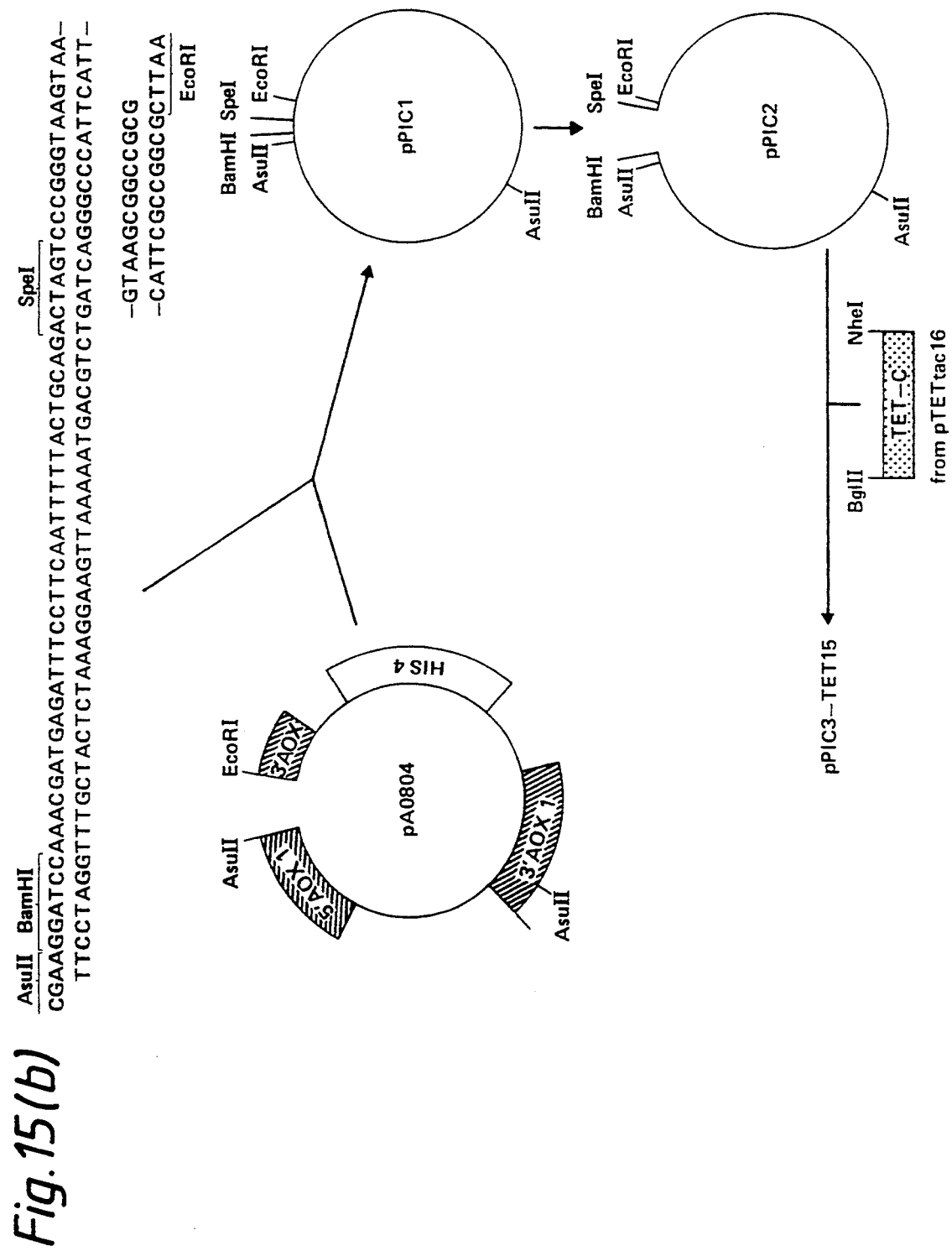

FIG. 15(a)-15(b) shows the construction of pP1C3-TET15. The oligonucleotides inserted in pA0804 to obtain pPIC1 are shown in SEQ ID NOS: 12 and 13.

Figure 16A:
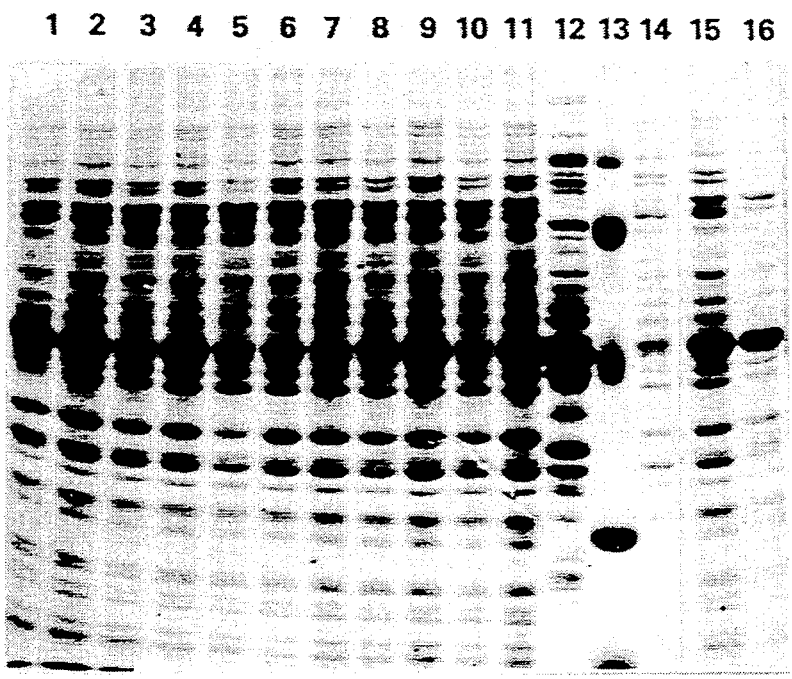
Figure 16B:
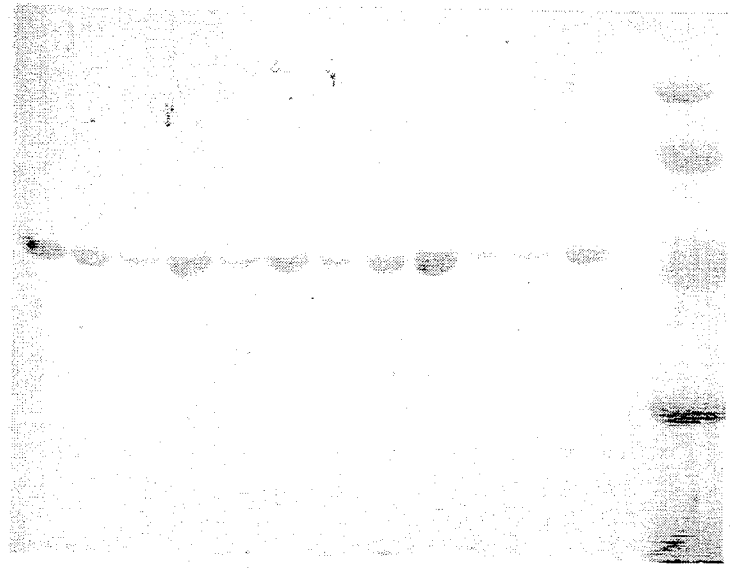

FIG. 16(a)-16(b) shows fragment C production in different pP1C3-TET15 transformants. Part a) shows proteins from total cell extracts separated on a Coomassie blue stained SDS-polyacrylamide gel. Lanes 1-11 are loaded with extracts from clones 885C, 887C, 8811C, 8812D, 881D, 882E, 885E, 8811E, 881F, 8810F, 883H respectively. Lane 12, extract from fragment C expressing E.coli. Lane 13, molecular weight markers (phosphorylase b, 97,400; bovine serum albumin, 68,000; ovalbumin, 43,000; chymotrypsinogen, 25,700; lactoglobulin, 18,400). Lane 14, insoluble fraction from 881F. Lane 15, total extract from 881F. Lane 16, soluble fraction from 881F. Part b) shows a Western blot of these samples. Lanes 1-9, as in part a). Lane 10, extract from 889F. Lane 11, extract from 8810F. Lane 12, extract from 883H. Lane 13, extract from untransformed cells. Lane 14, molecular weight markers.

Figure 17:
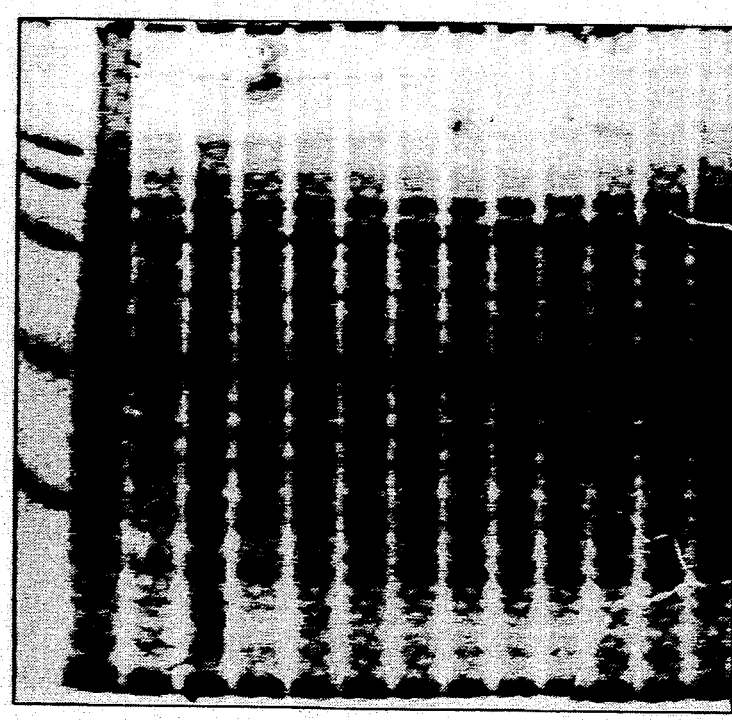

FIG. 17 shows a Coomassie blue stained SDS polyacrylamide gel showing fragment C production in a high cell density fermentation of clone 881F. Lane 1, molecular weight markers (β-galactosidase, 116,000; phosphorylase b, 97,400; bovine serum albumin, 68,000; ovalbumin, 43,000; carbonic anhydrase, 29,000). Lane 2, untransformed cell extract. Lane 3, 881F extract from an induced shake-flask culture. Lanes 4-14, extracts from cells taken from the fermenter at the following time intervals with respect to the beginning of induction, -15,0,2,4,6,8,24,28,30,32,52 hours.

The following Examples illustrate the present invention and are not intended to limit the invention in any way.

EXAMPLE 1

1. Construction of yeast expression vector pWYG7

Figure 1:
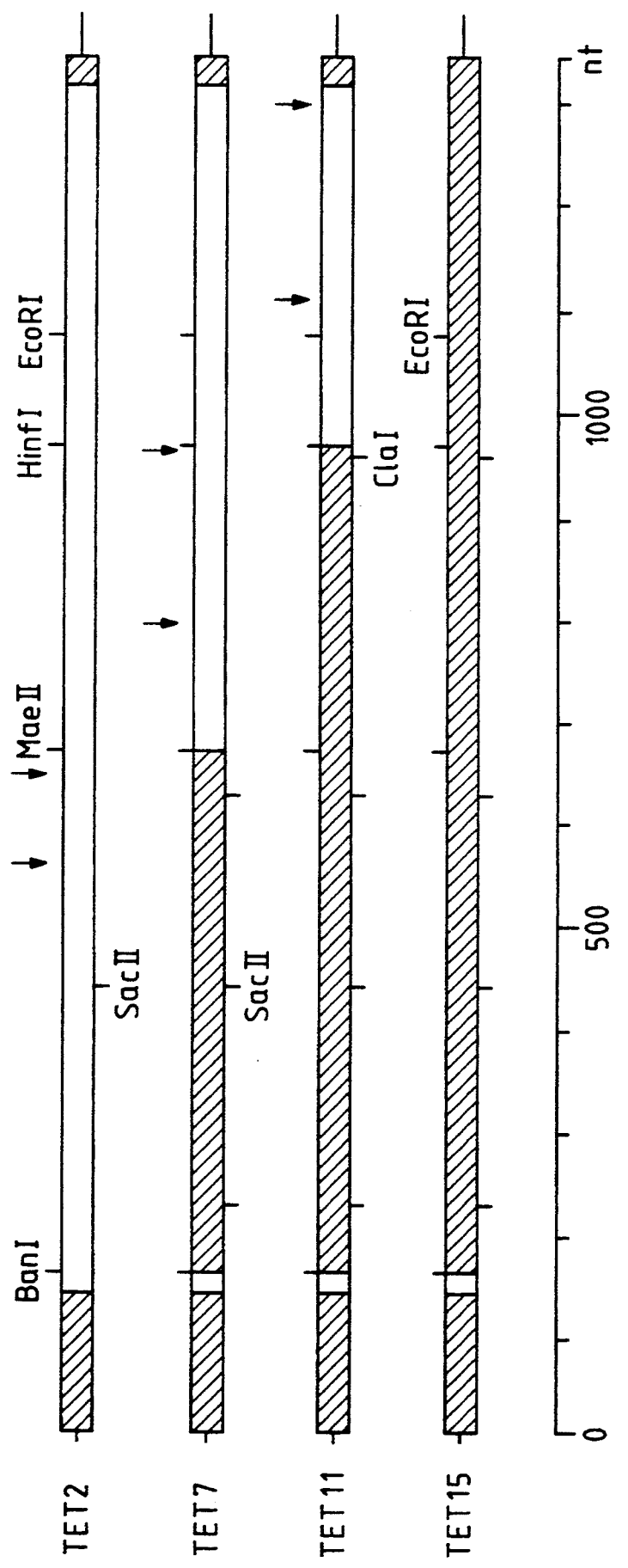
Figure 3:
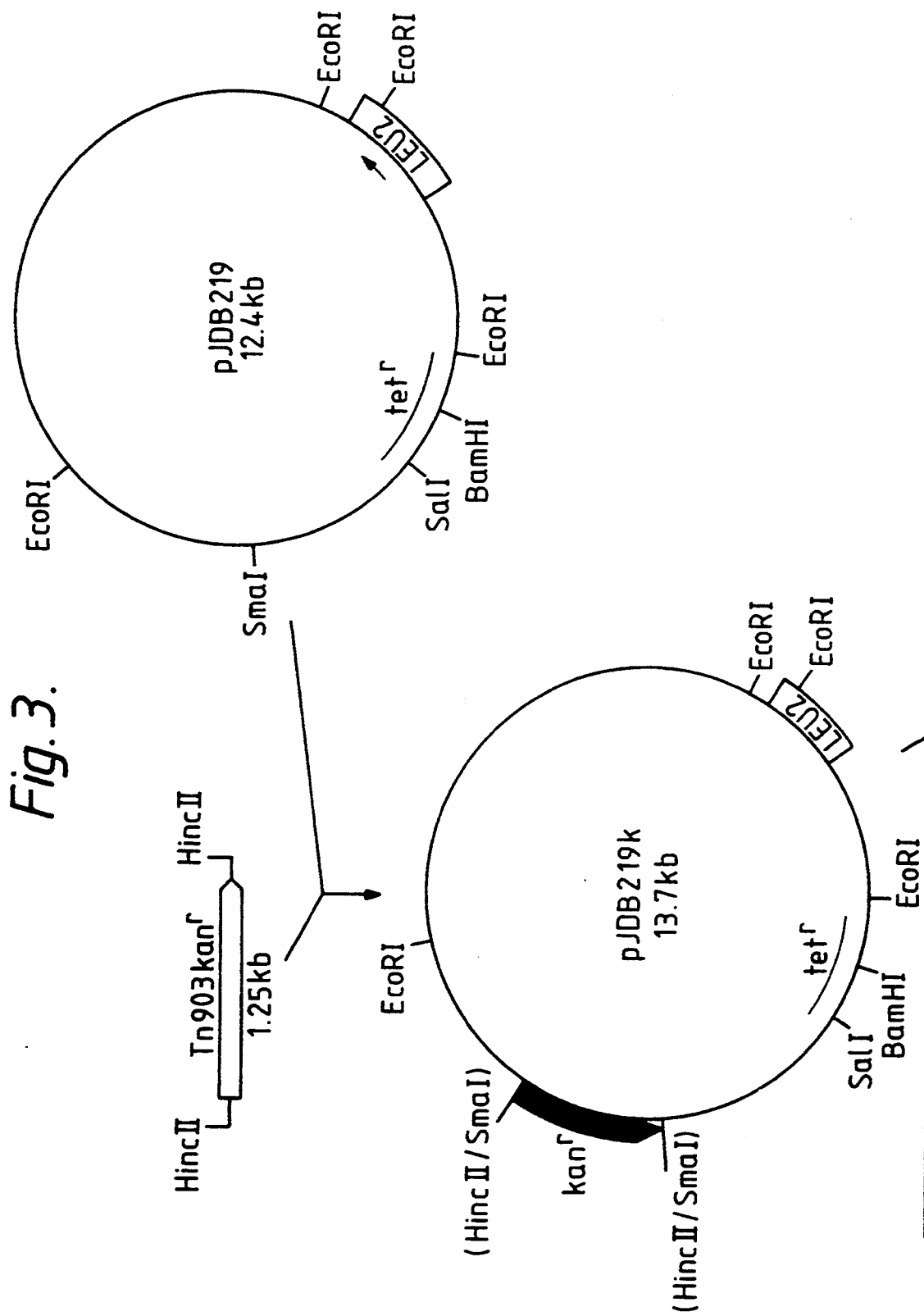
FIG. 3 shows the construction of the yeast expression vector pWYG 7. Foreign genes are inserted between the Bam HI and Bcl I sites.

The vector pWYG7, (Beesley, K. M., et al., Bio/Technology, 8, 644-649 (1990)), constructed at Wellcome, was used for the expression of C fragment. The construction of pWYG7 is outlined in FIG. 3. It is derived from the 2u vector pJDB219 (Beggs, J. D., Nature, 275, 104-109, (1978)) modified to contain a kanamycin-resistance marker (kan$^r$) and the yeast galactose-regulated GAL7 promoter. First the kan$^r$ marker (HincII fragment from pUC4K; Vieira, J., and Messing, J., Gene, 19, 259, (1982)) was ligated into the unique SmaI site of pJDB219 to give the kan$^r$ tet$^r$ vector pJDB219K. Secondly, a synthetic GAL7 promoter fragment (XhoI-BamHI fragment, sequence shown in FIG. 4 and in SEQ ID NO: 5) was cloned between the unique SalI and BamHI sites of pJDB219K. The resulting vector, pWYG7, has the GAL7 promoter with unique BamHI and BclI sites upstream of the yeast 2u plasmid FLP gene transcriptional terminator (Sutton, A., and Broach, J. R., Mol.Cell. Biol, 5, 2770-2780 (1985)). Foreign genes to be expressed from pWYG7 are inserted between the BamHI and BclI sites. The design of the GAL7 promoter fragment is discussed below.

The smallest fragment of DNA upstream of the GAL7 gene which exhibits full promoter activity has been defined by deletion mapping (Tajima, M., et al., Yeast, 1, 67-77, (1985)). Based on this information a 260bp GAL7 promoter fragment was synthesised (FIG. 4 for sequence). The 260bp promoter was synthesised as four overlapping oligonucleotides using a Pharmacia Gene Assembler (protocol supplied by Pharmacia). These oligonucleotides were phosphorylated and annealed using standard techniques, then ligated into XhoI-BamHI cut pIC-20H (Marsh, J. C., Gene, 32,481-485, (1984)). Positive clones were identified and their DNA sequenced using the double-stranded DNA sequencing method with universal and reverse sequencing primers (Hong, G. F., Biosc, Reports, 2, 907, (1982)). The sequence of the GAL7 inserts was confirmed, and then the XhoI-BamHI GAL7 insert was excised and cloned into pJDB219K as described above.

The design of the GAL7 promoter fragment in pWYG7 is such that the natural GAL7 DNA sequence has been slightly modified (2bp changed) in order to make the BamHI cloning site Upstream of the GAL7 mRNA start sites. The foreign gene to be expressed is then linked with synthetic DNA to the BamHI site, such that the GAL7 mRNA start sites are introduced, along with the GAL7 upstream untranslated sequences. Thus the first non-yeast DNA downstream of the promoter is the initiating ATG codon of the foreign gene, and the transcript produced will have a yeast GAL7 leader rather than a foreign leader which could reduce efficiency of translations.

EXAMPLE 2

Construction of yeast expression vector pWYG5

The vector pWYG5 is the same basic plasmid as pWYG7 but has the GAL1 promoter from pBM150 (Johnston, M. and Davis, R. W. Mol. Cell. Biol 4, 1440-1448 (1984)) in place of the GAL7 promoter. The 0.7kb EcoRI-BamHI fragment from pBM150, containing the divergent GAL and GAL10 promoters, was first sub-cloned between the EcoRI and BamHI sites of pIC-20H (Marsh et al., J. C., Gene, 32, 481-485, (1984)) to give pIC-GAL, then the 0.7kb XhoI-BamHI promoter fragment from pIC-GAL was isolated and placed between the SalI and BamHI sites of pJDB219K to give pWYG5 (the construction is outlined in FIG. 5).

The GAL1 promoter from pBM150 has a BamHI linker placed downstream of the RNA initiation sites and therefore pWYG5 is used differently from pWYG7. Foreign genes must be adapted to have a BamH1 or BamHI-compatible (i.e. BglII or BclI) site immediately upstream of the initiation codon. In order to conform with the consensus found in highly expressed yeast genes, the sequence upstream of the ATG should be rich in A residues and particularly have A at -3. As with pWYG7, the foreign genes are inserted between the BamHI and BclI sites of pWYG5.

EXAMPLE 3

Construction of E.coli expression vectors for tetanus toxin fragment C, including synthesised versions of the gene, and intermediate vectors for yeast expression.

Expression cassettes of fragment C DNA for transfer to the yeast vectors pWYG5 and pWYG7 were isolated from the E.coli expression vector pTETtac2 and its derivatives (Makoff et al., 1989; U.K. patent application No. 89141220.0,Ser. No. 07/777,337, filed Nov. 29, 1991. pTETtac2 is a tac promoter vector containing DNA coding for Met-fragment C (FIG. 6 for plasmid map); the first 161bp and last 42bp of the natural C.tetani DNA have been replaced by synthesised DNA which was altered to optimise codon usage for E.coli and to provide useful restriction sites. (All synthetic DNA was chemically synthesised as oligonucleotides of length 50–160, on a Pharmacia Gene Assembler, which were phosphorylated, annealed and assembled into the relevant plasmids). Expression vectors based on pTETtac2 were then constructed where progressively more of the C.tetani DNA, starting from the 5' end, was replaced by synthesised DNA whose codon usage was optimised for E.coli. The first vector pTETtac7, was constructed via the intermediate plasmid pTETtac6, shown in FIG. 7; pTETtac7 contains an approximately 45% synthesised gene. This involved cloning two oligonucleotides between the BanI and MaeII sites of pTETtac2 in order to produce the two unique sites NcoI and AflIII in pTETtac6. Eight more oligonucleotides were then cloned between the two sites to generate pTETtac11, which contained a 75% synthesised gene.

A version of pTETtac2 containing the 99% synthesised gene (pTETtac15) for fragment C was actually first designed specifically as an intermediate vector (pTETtac16) for transfer of the expression cassette to the yeast vector pWYG5. The nucleotide sequence of the synthesised gene is compared to the original C.tetani gene in FIG. 2 from this sequence and the restriction maps in FIG. 7 the sequence of each version of the gene can be derived. The overall scheme for the construction of pTETtac16 is shown in FIG. 8. First, pTETtac7 was modified by replacement of the DNA between the BglII and SalI sites with oligonucleotides which provided upstream sequences compatible with the yeast vector pWYG5 (sequence of oligonucleotides in FIG. 8 and in SEQ ID NOS: 6 and 7). Secondly, the remaining 400bp of the DNA encoding fragment C was synthesised as four oligonucleotides of length 140 to 160. These were phosphorylated, annealed and cloned between the ClaI and BamHI sites of pIC-20H. Recombinant plasmids containing the 400bp insert were identified and further checked by sub-cloning into M13 and sequencing (Sanger. F., et al., Proc.Nat.Acad. Sci., 74, 5463–5467, (1977)). A plasmid with an insert of the correct sequence, designated pIC-TET, was used as a source of the 400bp ClaI-BamHI fragment to ligate to the 4199bp AflIII-BamHI fragment of pTETtac14 and the 325bp AflIII-ClaI fragment of pTETtac11 in order to create pTETtac16. pTETtac16 then has the fully synthesised gene for fragment C with codons optimised for E.coli and considerably more (GC)-rich DNA than the C.tetani DNA, preceded by an upstream region suitable for expression in pWYG5.

EXAMPLE 4

Construction of yeast intracellular expression vectors for fragment C.

Four vectors were constructed, one based on pWYG7 and three on pWYG5. The pWYG7 vector, pWYG7-TET2, contained the largely unaltered form of the natural C.tetani gene from pTETtac2. The remaining vectors, pWYG5-TET7, pWYG5-TET11 and pWYG5-TET15 were all based on pWYG5 and contained the genes with progressively more synthesised DNA, from the plasmids pTETtac7, pTETtac11 and pTETtac16, respectively. Vector pWYG5-TET15 was deposited on 16th Feb. 1993 under the Budapest Treaty at the National Collection of Industrial and Marine Bacteria, Aberdeen, United Kingdom under accession number NCIMB 40538.

(i) pWYG7-TET2

Figure 9B:
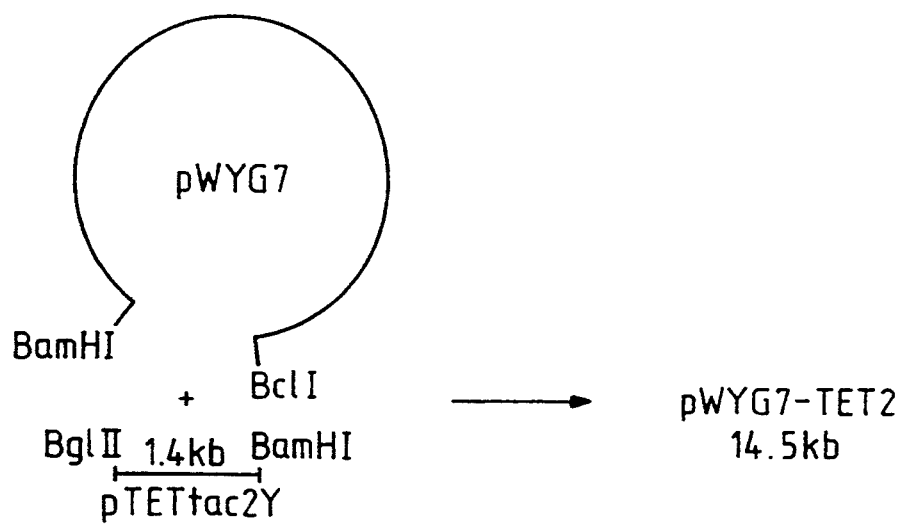

The DNA between the BglII and SalI sites of pTETtac2 was replaced by two oligonucleotides to give pTETtac2Y in order to provide the GAL7 upstream sequences required for expression in pWYG7 (FIG. 9 for construction and sequences; sequences also shown in SEQ ID NOS: 8 and 9). The oligonucleotides also placed an NcoI (CCATGG) site at the initiating ATG, altering the second codon from Lys to Val. The 1.4kb BglII-BamHI fragment from pTETtac2Y was isolated and ligated with pWYG7 (dam-DNA) which had been digested with the BamHI and bclI and then with calf intestinal alkaline phosphatase. Recombinant plasmids with inserts of the correct orientation were designated pWYG7-TET2.

Western blot analysis of protein extracts from induced cells containing pWYG7-TET2 gave no detectable product reacting with the antibody (track 2, FIG. 10). An ELISA quantitation gave an exceedingly low, but positive, figure of less than $10^{-3}$ of soluble protein. Since the gene for fragment C was found to be efficiently expressed in a number of other host cells, the plasmid and transformants were rechecked and expression re-analysed extensively.

A gene encoding an unmodified fragment C was next tested.

(ii) pWYG5-TET7 and pWYG5-TET11

These plasmids were made by transferring the 1.4kb BglII-BamHI fragments from pTETtac7 and pTETtac11 into pWYG5, between the BamHI to BclI sites. The transcripts produced by pWYG5-TET7 and pWYG5-TET11 in yeast may be translated sub-optimally since the upstream regions between the BglII site and the initiation codon are designed for E.coli expression, and do not conform to the consensus for highly expressed yeast genes.

Western blot analysis of the products from induced cells containing the plasmid pWYG5-TET7 showed the presence of two faint bands at approximately 29kDa and 30kDa (track 3, FIG. 10 - too faint to see in reproduction), but no full length fragment C (approximately 50kDa).

This result provided the clue that incomplete transcripts were being produced, therefore the fragment C-specific mRNA from pWYG7-TET2 and pWYG7-TET7 was analysed. The Northern blot (FIG. 11) showed that instead of a full-length transcript (expected size approximately 1655 nucleotides), pWYG7-TET2 gave rise to a major band of approximately 700 nt and a minor band of 600 nt and pWYG7-TET7 to two bands of approximately 900 and 1100 nt. Since these RNAs all hybridised to a probe from the 5' end of the gene (BglII to NcoI fragment from pTETtac7), incomplete transcripts were being produced within the gene for fragment C. The fact that the transcripts from pWYG-TET7 are larger suggests that the original C.tetani DNA contained sequences which do not allow the production of complete mRNA transcripts, and that these were destroyed as the DNA was synthesised. This idea is reinforced by the fact that the approximate position of the elements involved with the production of an incomplete mRNA transcript in pWYG7-TET2 is within the region which was modified by synthesis in pWYG5-TET7.

Induced cells containing pWYG5-TET11 were shown to produce fragment C of the correct size on Western blots (FIG. 10), at a concentration of approximately0.5% of cell protein. The product was soluble in that it remained in the supernatant after centrifugation at 10,000 g for 15 min.

An analysis of RNA from pWYG5-TET11 (FIG. 11) showed that there were two major transcripts of less than full length (1200 and 1400 nt), and only a minor amount of the full length transcript (approximately 1700 nt). Thus efficient expression was still being prevented by the remaining 400bp of *C.tetani* DNA in the pWYG5-TET11 plasmid.

(iii) pWYG5-TET15

The 1.4kb BglII-BamHI fragment of pTETtac16 was isolated and cloned between the BamHI and BclI sites of pWYG5 as described above.

Plasmids with inserts of the correct orientation were designated pWYG5-TET15 (FIG. 12).

Cells containing this plasmid produced greater amounts of fragment C than before, to a level of 2.5% of cell protein (ELISA quantitation and see FIG. 10). Analysis of the RNA indicated that for the first time most of the fragment C-specific RNA was full length (FIG. 11). Thus it must be concluded from the RNA analysis that the *C.tetani* DNA encoding fragment C contains at least six elements which are fully or partially responsible for the production of incomplete transcripts in yeast. The positions of the elements are shown in FIG. 1. With the present state of knowledge about transcription of mRNA in yeast few if any of these could be predicted from the sequence of the DNA, and they could be removed by re-synthesising the DNA to have a higher (G+C)-content. Alternatively, the elements could be accurately delineated by mapping of the 3' ends of the truncated transcripts described above, and only those regions identified as being responsible for the production of incomplete transcripts being resynthesised.

EXAMPLE 5

Construction of yeast secretion vectors for fragment C

Two vectors were constructed for the secretion of fragment C, pWYG9-TET2 and pWYG59-TET15. These both contained DNA encoding the prepro leader peptide from the yeast mating pheromone, alpha-factor (Kurjan, J. and Herskowitz, I., Cell, 30, 933–948, (1982)).

(i) pWYG9-TET2

This vector is similar to pWYG7-TET2 but contains the coding region for the alpha-factor leader peptide between the BamHI site of the GAL7 promoter and the NcoI site at the initiating ATG codon of fragment C. The synthetic DNA fragment contains altered codons, in order to generate a XhoI restriction site to facilitate cloning, giving a conservative amino acid change (Asp to Glu) immediately upstream of the KEX2 cleavage site. GAL7 upstream sequences required for expression in pWYG7 are also included (FIG. 13).

In Western blots of culture supernatants from cells transformed with pWYG9-TET2 a broad smear of reactive material of heterogenous molecular weight (75–200kD) was observed. When de-glycosylated with endoglycosidase H the molecular weight of this was substantially reduced to a major species of approximately 26kD (FIG. 14). This result gave further support for the notion that the wild-type C.tetani fragment C gene contains sequences fortuitously recognised as being responsible for the production of incomplete mRNA transcripts. The size of this band is consistent with it being a run-off translation product of the major transcript characterised by Northern analysis (Example 4).

(ii) pWYG59-TET15

This vector is similar to pWYG5oTET15 but contains the alpha-factor leader peptide coding region between the BamHI site of the GAL1 promoter and the SalI site near the 5' end of the fragment C gene. The synthetic DNA fragment also contains the same NcoI site found at the initiator ATG of pWYG7-TET2 (see FIG. 13).

Two forms of fragment C were found to be secreted into the medium by cells containing pWYG59-TET15. A diffuse band of high molecular weight material was detected similar to that seen with pWYG9-TET2. In addition, a major band of about 65kD was detected (FIG. 14). A ladder of at least four other less intense bands of lower molecular weight was also visible. All of these species were reduced to approximately 50kD, the size expected for correctly processed full length fragment C, when treated with Endo H suggesting that the differences between them are due to differences in N-linked glycosylation. Fragment C contains seven potential sites for the addition of asparagine-linked carbohydrate and our data suggests that at least five of these are actually being used during alpha-factor signal directed secretion.

Secretion of full length fragment C by yeast cells containing the resynthesised TET15 gene was found to be efficient. The total amount of fragment C secreted to the medium by unoptimised shake flask cultures was estimated to be about 7μg/ml and none was detected in intracellular extracts from these cultures.

EXAMPLE 6

Construction of *Pichia pastoris* intracellular expression vectors for fragment C.

The vector pPIC3-TET15, which is derived from pA0804, was used for intracellular expression of fragment C in Pichia (Diagan, et al., Dev. Ind. Microbiol., 29, 59–65, (1988); Sreekrishna et al., Biochemistry, 28, 4117–4125 (1989)). This vector uses the promoter from the AOX1 gene to drive expression and can be integrated into the host chromosomal AOX1 locus.

To facilitate insertion of the fragment C gene the synthetic adapter oligonucleotides shown in FIG. 15 and in SEQ ID NOS: 12 and 13 were cloned between the AsuII and EcoRI sites of pA0804, to give pPIC1. A derivative of this plasmid, pPIC2, which lacks the EcoRI site was then constructed. This was done by digesting with EcoRI followed by filling in of the protruding single stranded ends with the Klenow fragment of DNA polymerase I and the blunt ends were then ligated together. The 1.4kb BglII-NheI fragment from pTETtac16 containing the fragment C gene was then inserted between the BamH1 and SpeI sites of pPIC2 to give pPIC3-TET15 as shown in FIG. 15.

Fragment C production in shake flasks, by several pPIC3-TET15 transformants that grew slowly on methanol, was examined. FIG. 16 shows SDS-PAGE and Western blotting analysis of cell lysates. Expression levels were estimated by densitometric scanning of Coomassie blue stained gels and by ELISA and these varied between different transformants from 0.3% of total cell protein to about 11%. Even at the highest level of expression the product was soluble. The highest expressing strain, 881F, was used in high cell density inductions in a fermenter. Cells were grown to a density of 90g/l (dry weight) before induction. A time course for the induction is shown in FIG. 17. Production of fragment C began rapidly upon induction, rose to a level of about 20-28% of total cell protein after 24 hrs and remained at this level up to 52 hrs after induction. The final level of fragment C in the fermenter was estimated to be about 11g/l and again the product was soluble.

EXAMPLE 7

Transformation of yeast with fragment C expression vectors

The vectors were introduced into the *Saccharomyces cerevisae* strain S150-2B (a leu2 his3 ura3 trpl; (McCleod, M., et al., Cold Spring Harbor Symp., Quant., Biol., 49, 779–787, (1984)) using the lithium transformation procedure of Ito et al. J. Bact., 153, 163–168, (1983). Transformed yeast cells were incubated in YPD broth (Sherman, F., et al., Methods in Yeast Genetics, Cold Spring Harbour, N.Y., 1983) at 30° C. overnight prior to plating out on selective medium (YPD plus 500 ug/ml G418). This allows expression of G418-resistance and increases transformation frequency. Colonies that came up as $G418^r$ were tested on minimal medium lacking leucine (YNB, Difco+-glucose+histidine+uracil+tryptophan, Sherman et al., 1983) to test for the $Leu^+$ phenotype also conferred by the plasmids. Positive transformants ($G418^r$ $Leu^+$) were used for expression analysis.

The vector pPIC3-TET15 was introduced into *Pichia pastoris* strain GS115 using the sphaeroplast transformation procedure described by Cregg et al, (1985). (Cregg et al., Molecular and Cellular Biology, 5, 3376–3385 (1985)) To direct integration into the host chromosomal AOX1 locus the vector was digested with Bgl II and then mixed, in the presence of calcium ions and polyethylene glycol, with sphaeroplasts generated by enzymatic digestion of the cell walls with zymolyase. Transformed sphaeroplasts were regenerated in osmotically buffered agarose containing YNB, glucose (2%), sorbitol (1%) biotin (400 μg/1) and His-assay medium (Difco). Transformed cells were tested for growth on methanol since those disrupted at AOX1 by insertion of the vector should grow slowly on methanol.

EXAMPLE 8

Galactose induction and preparation of cell lysates

Transformants were grown to the mid-logarithmic stage ($10^7$ cells/ml) in YP broth containing 2% raffinose and 500 μg/ml G418 at 30° C. in an orbital shaker. An aliquot of 40% galactose was then added to a final concentration of 2% and the culture was incubated for a further 24h. The cells were harvested by low speed centrifugation, washed once in distilled water, and resuspended in ice-cold break buffer (20 mM sodium phosphate pH7.0, 0.1% triton X-100, 4 mM phenylmethyl sulphonyl fluoride, 4 mM EGTA, and 2μg/ml each of pepstatin, antipain, leupeptin and chymostatin; 5ml for cells from a 250ml culture). Acid-washed glass beads (0.45mm) were added and the cells were broken by vigorous vortexing. In order to remove insoluble proteins, the crude cell lysate could be cleared by centrifugation for 15 min at 10,000 g. The protein concentration of the extracts was determined using the BioRad protein assay (BioRad, according to manufacturer's instructions) and the material was stored at −70°.

EXAMPLE 9

Methanol Induction of Pichia cultures.

Transformants were grown at 30° C. overnight to saturation in liquid minimal medium (YNB containing biotin, 400 μg/l, and glycerol, 2% v/v). lml aliquots of these cultures were used to inoculate shake flasks containing 10 mls of the same medium plus 1% casamino acids. After 6–8 hrs incubation at 30° C. the cells were harvested by centrifugation and resuspended in YNB (Difco) containing biotin (400 μg/l) casamino acids (1%), and methanol (0.5% v/v). After further incubation for 2-6 days the cells were harvested and lysates prepared as described for Saccharomyces (see Example 8).

Production of fragment C by high cell density *Pichia pastoris* cultures was carried out using a 21 Braun fermenter equipped with monitors and controls for pH, dissolved $O_2$, stirring speed, temperature and air flow. A 10ml YNB+biotin+2% glycerol overnight culture was used to inoculate the fermenter containing 1 litre of 5X basal salts (phosphoric acid, 42 mls/l; calcium sulphate.$2H_2O$. 1.8 g/l; potassium sulphate, 28.6 g/l; magnesium sulphate.$7H_2O$, 23.4 g/l; potassium hydroxide, 6.5 g/l) with 4mls of $PTM_1$ salts (cupric sulphate.$5H_2O$, 6 g/l; potassium iodide, 0.08 g/l; manganese sulphate.$H_2O$, 3 g/l; sodium molybdate, 0.2 g/l; boric acid, 0.02 g/l; cobalt chloride, 0.5 g/l; zinc chloride, 20 g/l; ferrous sulphate.$7H_2O$, 65 g/l; biotin, 0.2 g/l; sulphuric acid 5 mls/l) and 5% (v/v) glycerol at 30° C. Dissolved $O_2$ was maintained above 20% by adjusting aeration and agitation, and the pH was maintained at pH5.0 by the addition of 50% (v/v) ammonium hydroxide. Growth was continued until the glycerol was exhausted (24–30 hrs). A limited glycerol feed (containing 50% w/v glycerol and 12 ml/l $PTM_1$ salts) was then initiated at 12 mls/hr for 17–21 hrs. After this period the culture was induced by replacing the glycerol feed with a methanol feed (100% methanol plus 12 ml/l $PTM_1$ salts) at 1 ml/hr. for 2 hrs. Then the methanol feed rate was gradually increased over a period of 6 hours to 6 mls/hr and the fermentation was continued using these conditions for a further 46–92 hrs.

EXAMPLE 10

Concentration of culture supernatants and glycoprotein analysis

Cells were induced and then harvested by centrifugation as described in Example 8. Culture supernatants were concentrated by ultrafiltration using Centricon 30 microconcentrators (Amicon), centrifuging at 4,000g for 45'. Supernatants from larger scale cultures were concentrated by ultrafiltration with Amicon PM30 membranes using a stirred cell. N-linked oligosaccharides were removed by digestion of concentrated supernatants with Endoglycosidase H (Endo H, Boehringer Mannhelm). Aliquots (25 µl) were taken and 5 µl of digestion buffer added (0.2M NaH$_2$PO$_4$, 10 mM B-mercaptoethanol, 1% SDS). After boiling for 5 minutes samples were cooled on ice and protease inhibitors added to the same final concentrations as given above (Example 8). Endo H (9 mU) was added and the samples were incubated for 18hrs at 37° C. before analysis by SDS-PAGE (Example 11).

EXAMPLE 11

SDS-polyacrylamide gel analysis of proteins

Soluble or total protein extracts from induced yeast cells were separated by electrophoresis in SDS-polyacrylamide gels (Laemmli, UK., Nature, 227, 680–685, (1970)). The proteins in the gel could be visualised by staining with Coomassie Brilliant Blue R. Alternatively the proteins were transferred to a nitrocellulose filter and reacted with rabbit antiserum to fragment C (isolated from C.tetani) and then goat anti-rabbit IgG conjugated to horse-radish peroxidase followed by colour development with hydrogen peroxide and 4-chloronaphthol (BioRad). In this way the expressed fragment C could be specifically detected.

EXAMPLE 12

Immunoassay quantitation of fragment C

A two antibody sandwich enzyme-linked immunosorbent assay (ELISA) for fragment C was developed. Purified pepsinised antibody prepared from horses hyperimmunised with tetanus toxoid (Hughes et al., J. Appl.Bact. 38, 1974, 603–622) was used to coat flexible polyvinylchloride microtitre plates (Dynatech, Billinghurst, GB). Coating was performed overnight at 40° C. in 50 mM sodium carbonate pH 9.5 (12.5 μg pepsinised antibody per ml, 100 μl per well). Plates were washed three times with phosphate buffered saline pH 7.2, 0.12 (w/v) Tween (Trade Mark) 20 (PBS-Tween).

Non-specific binding was reduced by incubation of plates with PBS-Tween containing 12% (wt/vol) BSA or 5% (wt/vol) non-fat dry milk. Plates were then incubated sequentially with antigen, second antibody and anti-rat IgG peroxidase conjugate (Kinkegaard and Perry, Maryland, US) for 1 hr at 37° C. in each case. The second antibody was a rat monoclonal (TTO9) which binds with high affinity to fragment C (Sheppard et al., Infec. Immun. 43, 1984, 710–714) and it was used at a concentration of 2 μg/ml.

Anti-rat peroxidase conjugate was used at a dilution of 1:3000. Each reagent was diluted into PBS-Tween containing 5% non-fat dry milk prior to addition to plates. Plates were washed three times with PBS-Tween after each incubation. Bound enzyme complex was assayed using tetramethylbenzidine (TMB) as the chromogenic substrate. 1 mg TMB tablets (Wellcome Diagnostics) were dissolved in 10 ml of 0.0625M trisodium citrate containing 0.01% hydrogen peroxide. 100 μl of reagent was added to each well and the reaction terminated by addition of 100 μl 2M $H_2SO_4$ after incubation for 10–15 mins at room temperature. Plates were read using a Titertek multiscan plate reader (MCC/340) at 450 nm.

For quantitation, fragment C prepared from *C.tetani* (Fairweather, N., et al., J.Bact., 165, 21–27, (1986)) was used as a standard. Several dilutions of this fragment C gave a narrow range titration curve with a linear portion between about 1 μl/ml and 10 μg/ml. Titration curves for the recombinant fragment C were comparable, with similar slope and range to the standard curve. The titre of unknown samples were determined either by comparing the midpoints of titration curves or more routinely by reading directly from the linear portion of the standard curve.

Protein was determined using the BCA assay reagent (Pierce) with bovine serum albumin as protein standard.

EXAMPLE 13

Preparation and analysis of RNA from yeast cells

In order to prepare RNA, transformed yeast cells were grown in YP+2% raffinose+500 μg/ml G418 to a density of approximately $5\times10^5$ cells/ml, then induced for 24 hr after addition of 2% galactose. Total RNA was then prepared from the cells and analysed by Northern blotting as described previously (Romanos, M. A., and Boyd, A., Nucl. Acids Res., 16, 7333–7350, (1988)). The Northern blots were probed with fragments of pTETtac2 DNA, and its derivatives, labelled by the random priming method (Feinberg, A., and Vogelstein, B., Anal. Biochem, 132, 6–13, (1983)).

EXAMPLE 14

Immunisation of mice

Fragment C was purified from lysates of induced cells harbouring pWYG5-TET15 by affinity chromatography using TTO8 monoclonal antibody (Sheppard, A. J., et al., Infect. Immun., 43, 710–714 (1984)) linked to cyanogen bromide - activated sepharose 4B. Fragment C was eluted with 0.1M sodium citrate pH3.0 and neutralised by addition of one volume of 0.1M sodium phosphate pH7.0. Secreted fragment C was prepared by concentration of supernatants from induced cultures harbouring pWYG59-TET15 without further purification.

Vaccines containing fragment C were prepared with 10% Alhydrogel (trade mark) and serial dilutions were prepared. Balb/C mice were injected with 0.5ml then challenged four weeks later with 100 $LD_{50}$ of tetanus toxin. Survivors were counted after a further four days. The results, summarised in the table below, show that yeast intracellular fragment C has at least equal potency to *E.coli* produced material, whereas the secreted fragment C is inactive.

| Vaccine | Concentration of fragment C | Survivors |
|---|---|---|
| 1. Yeast intracellular fragment C | 50 μg/ml | 5 |
| | 12.5 μg/ml | 5 |
| | 3.125 μg/ml | 5 |
| | 0.78 μg/ml | 4 |
| 2. Yeast secreted fragment C | 50 μg/ml | 0 |
| | 12.5 μg/ml | 0 |
| | 3.125 μg/ml | 0 |
| | 0.78 | 0 |
| 3. *E. coli* fragment C | 25 μg/ml | 3 |
| | 6.25 μg/ml | 1 |
| | 1.5 μg/ml | 0 |
| 4. PBS (negative control) | 0 | 0 |

EXAMPLE 15

Immunisation of mice (also using secreted deglycosylated material)

Fragment C was purified from lysates of induced cells harbouring pWYG5-TET15 by affinity chromatography using TTO8 monoclonal antibody (Sheppard, A. J., et al., Infect. Immun., 43, 710–714 (1984)) linked to cyanogen bromide - activated sepharose 4B. Fragment C was eluted with 0.1M sodium citrate pH3.0 and neutralised by addition of one volume of 0.1M sodium phosphate pH7.0. Secreted fragment C was prepared by concentration of supernatants from induced cultures harbouring pWYG59-TET15 without further purification. To de-glycosylate this material for immunisation experiments the concentrate was treated with Endott as described in Example 10 except without the addition of mercaptoethanol and SDS and without boiling the sample.

Vaccines containing fragment C were prepared with 10% Alhydrogel (trade mark) and serial dilutions were prepared. Balb/C mice were injected with 0.5ml then challenged four weeks later with 100 $LD_{50}$ of tetanus toxin. Survivors were counted after a further four days. The results, summarised in the table below, show that yeast intracellular fragment C was at least as effective as the *E.coli* derived material, which has previously been shown to be equivalent to *C.tetani* fragment C (Makoff et al., 1989a). In contrast, the secreted product was totally inactive. However, de-glycosylation of secreted fragement C with endo H rendered it as protective as the intracellular product, syggesting that important neutralising epitopes were masked by carbohydrate side-chains in the glycosylated form.

Protection of immunised mice against tetanus toxin challenge

| | Survivors after challenge[a] | | | | |
|---|---|---|---|---|---|
| Antigen (dose in μg) | 2 | 0.5 | 0.125 | 0.03 | 0.008 |
| *E. coli* fragment C | 4[b] | 2 | 0 | 0 | 0 |
| Yeast intracellular | 5 | 5 | 5 | 0 | 0 |
| Yeast secreted | 0 | 0 | 0 | 0 | 0 |
| Yeast secreted, de-glycosylated | 5 | 5 | 3 | 0 | 0 |
| Saline | 0 | | | | |

[a]Groups of five mice were challenged with 100 $LD_{50}$ of tetanus toxin.
[b]Four mice in this group.

What we claim is:

1. An expression vector which incorporates DNA encoding tetanus toxin fragment C having the amino acid sequence shown in SEQ ID NO:2 and having an increased (G+C)-content relative to the wild-type DNA sequence show in SEQ ID NO:1 in each of the following regions:
  (i) from nucleotide 510 to nucleotide 710,
  (ii) from nucleotide 650 to nucleotide 850,
  (iii) from nuceotide 800 to nucleotide 1100,
  (iv) from nucleotide 900 to nucleotide 1200 and,
  (v) from nucleotide 1100 to nucleotide 1356.
the numbers corresponding to those set forth in the sequence of SEQ ID NO:1 so as to allow the production of complete mRNA transcripts in yeast, which vector thereby expresses said fragment C in yeast, wherein the said DNA is as shown in SEQ ID NO:3.

2. A yeast organism transformed with an expression vector which incorporates DNA encoding tetanus toxin fragment C having the amino acid sequence shown in SEQ ID NO:2 and having an increased (G+C)-content relative to the wild-type DNA sequence shown in SEO ID NO:1 in each of the following regions:
  (i) from nucleotide 510 to nucleotide 710,
  (ii) from nucleotide 650 to nucleotide 850,
  (iii) from nucleotide 800 to nucleotide 1100,
  (iv) from nucleotide 900 to nucleotide 1200 and,
  (v) from nucleotide 1100 to Nucleotide 1356, the numbers corresponding to those set forth in the sequence of SEO ID NO:1, so as to allow the production of complete mRNA transcripts in yeast, which vector thereby expresses said fragment C in yeast, wherein the said DNA is as shown in SEQ ID NO:3.

3. A process for the preparation of fragment C of tetanus toxin, which comprises the culturing of a yeast organism transformed with an expression vector which incorporates DNA encoding tetanus toxin fragment C having the amino acid sequence shown in SEQ ID NO:2 and having an increased (G+C)-content relative to the wild-type DNA sequence shown in SEQ ID NO:1 in each of the following regions:
  (i) from nucleotide 510 to nucleotide 710,
  (ii) from nucleotide 650 to nucleotide 850,
  (iii) from nucleotide 800 to nucleotide 1100,
  (iv) from nucleotide 900 to nucleotide 1200 and,
  (v) from nucleotide 1100 to nucleotide 1356,
the numbers corresponding to those set forth in the sequence of SEO ID NO:1, so as to allow the production of complete mRNA transcripts in yeast, which vector thereby expresses said fragment C in yeast, wherein the said DNA is as shown in SEQ ID NO: 3.

* * * * *